US007250558B2

(12) United States Patent
Famodu et al.

(10) Patent No.: US 7,250,558 B2
(45) Date of Patent: Jul. 31, 2007

(54) DISEASE RESISTANCE FACTORS

(75) Inventors: Omolayo O. Famodu, Newark, DE (US); Jian-Ming Lee, West Caldwell, NJ (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/002,562

(22) Filed: Dec. 2, 2004

(65) Prior Publication Data

US 2005/0102715 A1 May 12, 2005

Related U.S. Application Data

(63) Continuation of application No. 10/009,791, filed as application No. PCT/US00/11956 on May 3, 2000, now abandoned.

(60) Provisional application No. 60/133,041, filed on May 7, 1999.

(51) Int. Cl.
*A01H 1/00* (2006.01)
*C07H 21/04* (2006.01)
*C07K 14/415* (2006.01)
*C12N 5/14* (2006.01)
*C12N 9/00* (2006.01)

(52) U.S. Cl. .................. 800/295; 435/6; 435/69.1; 435/468; 435/419; 435/252.3; 435/320.1; 435/183; 530/370; 536/23.6; 800/278

(58) Field of Classification Search .................. 435/6, 435/69.1, 468, 419, 252.3, 320.1, 183; 530/370; 536/23.6; 800/278, 295, 296
See application file for complete search history.

(56) References Cited

FOREIGN PATENT DOCUMENTS

| WO | WO 91/18512 A1 | 12/1991 |
| WO | WO 98/00023 A2 | 1/1998 |
| WO | WO 98/39422 A1 | 9/1998 |

OTHER PUBLICATIONS

B. Kobe et al., "The leucine-rich repeat as a protein recognition motif," Current Opinion in Structural Biology, vol. 11, pp. 725-732, 2001.
D.-X. Xie et al., "COI1: An *Arabidopsis* Gene Required for Jasmonate-Regulated Defense and Fertility," Science, vol. 280, pp. 1091-1094, May 15, 1998.
A. Devoto et al., "COI1 links jasmonate signalling and fertility to the SCF ubiquitin-ligase complex in *Arabidopsis*," The Plant Journal, vol. 32, pp. 457-466, 2002.
A. Bateman et al., "The Pfam Protein Families Database," Nucleic Acids Research, vol. 20, No. 1, pp. 276-280, 2002.
E. Kipreos et al., "The F-box protein family," Genome Biology, vol. 1, No. 5, pp. 3002.1-3002.7, Nov. 10, 2000.
L. Li et al., "The Tomato Homolog of Coronatine-Insensitive1 Is Required for the Maternal Control of Seed Maturation, Jasmonate- Signaled Defense Responses, and Glandular Trichome Development," The Plant Cell, vol. 16, pp. 126-143, Jan. 2004.
EMBL Database Sequence Listing Accession No. AW061660, Oct. 6, 1999, V. Walbot, Maize ESTs From Various CDNA Libraries Sequenced at Stanford University.
EMBL Database Sequence Listing Accession No. AQ161346, Sep. 9, 1998, R. A. Wing et al., A BAC End Sequencing Framework to Sequence the Rice Genome.
EMBL Database Sequence Listing Accession No. AW054624, Sep. 26, 1999, V. Walbot, Maize ESTs From Various CDNA Libraries Sequenced at Stanford University.
EMBL Database Sequence Listing Accession No. AF036340, May 29, 1998, B. J. Feys et al., *Arabidopsis* Mutants Selected for Resistance to the Phytotoxy Are Male Sterile, Insensitive to Methyl Jasmonate, and Resistant to Bacterial Pathogen.
EMBL Database Sequence Listing Accession No. AI444738, Mar. 18, 1999, V. Walbot, Maize Ests From Various CDNA Libraries Sequenced at Stanford University.
EMBL Database Sequence Listing Accession No. AUO32235, Oct. 19, 1998, Yamamoto, K. et al., Rice CDNA From Root.
Celso E Benedetti et al., Plant Phys., vol. 116:1037-1042, 1998, Differential Expression of a Novel Gene in Response to Coronatine, Methyl Jasmonate, and Wounding in the COI1 Mutant of *Arabidopsis*.
Iris A.M.A. Pennickx et al., Plant Cell, vol. 10:2103-2113, 1998, Concomitant Activation of Jasmonate and Ethylene Response Pathways is Required for Induction of a Plant Defensin Gene in *Arabidopsis*.
Bart P.H.J. Thomma et al, PNAS, vol. 95:15107-15111, 1998, Separate Jasmonate-Dependent and Salicylate-Dependent Defense-Response Pathways in *Arabidopsis* are Essential for Resistance to Distinct Microbial Pathogens.
EMBL Database Sequence Listing Accession No. U77346, Apr. 19, 1997, J. Gray et al, A Novel Suppressor of Cell Death in Plants Encoded by the LIS1 Gene of Maize.
EMBL Database Sequence Listing Accession No. U77345, Apr. 18, 1997, A Novel Suppressor of Cell Death in Plants Encoded by the LIS1 Gene of Maize.
John Gray et al., Cell, vol. 89:25-31, 1997, A Novel Suppressor of Cell Death in Plants Encoded by the LIS1 Gene of Maize.
Dao-Xin Xie et al., Science, vol. 280:1091-1094, 1998, COI1: An *Arabidopsis* Gene Required for Jasmonate-Regulated Defense and Fertility.
Bart J.F. Feys et al., Plant Cell, vol. 6:751-759, 1994, *Arabdiopsis* Mutants Selected for Resistance to the Phytotoxy Are Male Sterile, Insensitive to Methyl Jasmonate, and Resistant to Bacterial Pathogen.

(Continued)

*Primary Examiner*—Phuong T. Bui

(57) ABSTRACT

This invention relates to an isolated nucleic acid fragment encoding a disease resistance factor. The invention also relates to the construction of a chimeric gene encoding all or a substantial portion of the disease resistance factor, in sense or anti-sense orientation, wherein expression of the chimeric gene results in production of altered levels of the disease resistance factor in a transformed host cell.

10 Claims, 6 Drawing Sheets

OTHER PUBLICATIONS

Maria Jose Cordero et al, Plant J., vol. 6(2):141-150, 1994, Expression of a Maize Proteinase Inhibitor Gene is Induced in Response to Wounding and Fungal Infection: Systemic Would-Response of a Monocot Gene.

Carl Simmmons et al, Mol Plant-Microbe Int., vol. 11(11):1110-1118, 1998, The Maize Lethal Leaf Spot 1 Mutant Has Elevated Resistance to Fungal Infection at the Leaf Epidermis.

National Center for Biotechnology Information General Identifier No. 2088647, Apr. 5, 2000, X. Lin et al, Sequence and Analysis of Chromosome 2 of the Plant *Arabidopsis thaliana*.

Xiaoying Lin et al, Nature, vol. 401:761-768, 1999, Sequence and Analysis of Chromosome 2 of the Plant *Arabidopsis thaliana*.

National Center for Biotechnology Information General Identifier No. 3158394, May 28, 1998, B. J. Feys et al, *Arabidopsis* Mutants Selected for Resistance to the Phytotoxin Coronatine Are Male Sterile, Insensitive to Methyl Jasmonate, and Resistant to a Bacterial Pathogen.

National Center for Biotechnology Information General Identification No. 1935912, Apr. 24, 2001, J. Gray et al, A Novel Suppressor of Cell Death in Plants Encoded by the LIS1 Gene of Maize.

National Center for Biotechnology Information General Identifier No. 1935914, Apr. 15, 1997, T. Newman et al., Genes Galore: A Summary of Methods for Accessing Results From Large-Scale Partial Sequence of Anonymous *Arabidopsis* CDNA Clones.

Tom Newman et al, Plant Phys., vol. 106:1241-1255, 1994, Genes Galore: A Summary of Methods for Accessing Results From Large-Scale Partial Sequence of Anonymous *Arabidopsis* CDNA Clones.

National Center for Biotechnology Information General Identifier No. 7489721, Jul. 21, 2000, J. Gray et al., A Novel Suppressor of Cell Death in Plants Encoded by the LIS1 Gene of Maize.

Wang, Zhilong et al., GmCOI1, A Soybean F-Box Protein Gene . . . , MPMI, 2005, pp. 1285-1295, vol. 18, No. 12.

NCBI; http://www.ncbi.nlm.nih.gov/entrez/viewer.fcgi?db=nucleotide&val=3158393.

NCBI; http://www.ncbi.nlm.nih.gov/entrez/viewer.fcgi?db=protein&val=72154229.

Figure 1A

```
SEQ ID NO:18    ------------------------------------------------------------
SEQ ID NO:22    TKTSAPFLFTLSLRSNMTEERNVRKTRV-------VDVVLDCVIPYIDDPKDRDAVSQVC
SEQ ID NO:20    MGGEAP---------EARRLDRAMSFGGAGSIPEEALHLVLGYVDDPRDREAVSLVC
SEQ ID NO:37    M---------------EDPDIKRCKL--SCVATVDDVIEQVMTYITDPKDRDSASLVC
                1                                                           60

SEQ ID NO:18    ------------------------------------------------------------
SEQ ID NO:22    RRWYELDSLTRKHVTIALCYTTTPARLRRFPHLESLKLKGKPRAAMFNLIPEDWGGHVT
SEQ ID NO:20    RRWHRIDALTRKHVTVPFCYAASPAHLLARFPRLESLAVKGKPRAAMYGLIPEDWGAYAR
SEQ ID NO:37    RRWFKIDSETREHVTMALCYTATPDRLSRRFPNLRSLKLKGKPRAAMFNLIPENWGGYVT
                61                                                         120

SEQ ID NO:18    ----------------------------------TRPRT---------------------
SEQ ID NO:22    PWVKEISQYFDCLKSLHFRRMIVKDSDLQNLARDRGHVLHALKLDKCSGFTTDGLFHIGR
SEQ ID NO:20    PWVAELAAPLECLKALHLRRMVVTDDDLAALVRARGHMLQELKLDKCSGFSTDALRLVAR
SEQ ID NO:37    PWVTEISNNLRQLKSVHFRRMIVSDLDLDRLAKARADDLETLKLDKCSGFTTDGLLSIVT
                121                                                        180

SEQ ID NO:18    ------------------------------*--------*-------***-----*---
SEQ ID NO:22    --RGLETLFLEESTIDEKENDEWIRELATSNSVLETLNFFLTDL-RASPEYLTLLVRNCQ
SEQ ID NO:20    FCKSLRVLFLEESSILEKD-GEWLHELALNNTVLETLNFYLTDIAVKIEDLELLAKNCP
SEQ ID NO:37    SCRSLRTLFLEECSIADNGT-EWLHDLAVNNPVLETLNFHMTEL-TVVPADLELLAKKCK
                                                                           240
SEQ ID NO:37    HCRKIKTLLMEESSFSEKD-GKWLHELAQHNTSLEVLNFYMTEFAKISPKDLETIARNCR
                181
```

Figure 1B

```
SEQ ID NO:18   RLKTLKISECFMPDLVSLFRTAQTLQEFAGGSFEEQGQPVASRNYENYYFPPSLHRLSLL
SEQ ID NO:22   NLVSVKLTDCEILDLVNFFKHASALEEFCGGTYNE--E---PERYSAISLPAKLCRLGLT
SEQ ID NO:20   SLISLKISDCDFSDLIGFFRMAASLQEFAGGAFIEQGELT---KYGNVKFPSRLCSLGLT
SEQ ID NO:37   SLVSVKVGDFEILELVGFFKAAANLEEFCGGSLNE--DIGMPEKYMNLVFPRKLCRLGLS
                                                                        300

SEQ ID NO:18   YMGTNDMQILFPYATALKKLDLQFTFLSTEDHCQIVQRCSNLETLEVRDVIGDRGLQVVA
SEQ ID NO:22   YIGKNELPIVEMFAAVLKKLDLLYAMLDTEDHCMLIQRCPNLEVLETRNVIGDRGLEVLG
SEQ ID NO:20   YMGTNEMPIIFPFSALLKKLDLQYTFLTTEDHCQLIAKCPNLLLVLAVRNVIGDRGLGVVA
SEQ ID NO:37   YMGPNEMPILFPFAAQIRKLDLLYALLETEDHCTLIQKCPNLEVLETRNVIGDRGLEVLA
                                                                        360

SEQ ID NO:18   QTCKKLHRLRVERGDDDQGGLEDEQGRISQVGLMAIAQGCPELTYWAIHVSDITNAALEA
SEQ ID NO:22   RCCKRLRLKRLRIERGDDDQG-MEDEEGTVSHRGLIALSQGCSELEYMAVYVSDITNASLEH
SEQ ID NO:20   DTCKKLQRLRVERGDDDDPG-LQEEQGGVSQVGLTTVAVGCRELEYIAAYVSDITNGALES
SEQ ID NO:37   QYCKQLKRLRIERGADEQG-MEDEEGLVSQRGLIALAQGCQELEYMAVYVSDITNESLES
                                                                        420

SEQ ID NO:18   VGTCSKNLNDFRLVLLDREAHITELPLDNGVRALLRGCTKLRRFAFYVRPGALSDVGLGY
SEQ ID NO:22   IGTHLKNLCDFRLVLLDHEEKITDLPLDNGVRALLRGCDKLRRFALYLRRGGLTDVGLGY
SEQ ID NO:20   IGTFCKNLCDFRLVLLDREERITDLPLDNGVRALLRGCTKLRRFALYLRPGGLSDTGLGY
SEQ ID NO:37   IGTYLKNLCDFRLVLLDREERITDLPLDNGVRSLLIGCKKLRRFAFYLRQGGLTDLGLSY
                                                                        480
```

Figure 1C

```
                              *     *  **   *  *** *  *   *   *  *    *   *** 
SEQ ID NO:18    VGEFSKSIRYMLLGNVGESDNGIIQLSKGCPSLQKLEVRGC-LFSEHALALAALQLKSLR
SEQ ID NO:22    IGQYSPNVRWMLLGYVGESDAGLLEFAKGCPSLQKLEMRGCLFFSERALAVAATQLTSLR
SEQ ID NO:20    IGQYSGIIQYMLLGNVGETDDGLIRFALGCENLRKLELRSC-CFSEQALARAIRSMPSLR
SEQ ID NO:37    IGQYSPNVRWMLLGYVGESDEGLMEFSRGCPNLQKLEMRGC-CFSERAIAAAVTKLPSLR
                481                                                        540

*******   *    ** *    **  *  *   *  *       ********
SEQ ID NO:18    YLWVQGFRSSPTGTDIMAMVRPFWNIEYIVP------DQDEPCPEHKRQILAYYSLA
SEQ ID NO:22    YLWVQGYGVSPSGRDLLVMARPFWNIELI-PSRKVATNTNPDETVVVEHPAHILAYYSLA
SEQ ID NO:20    YVWVQGYKASKTGHDLMLMARPFWNIEFTPPSSENANRMREDGEPCVDSQAQILAYYSLA
SEQ ID NO:37    YLWVQGYRASMTGQDLMQMARPYWNIELI-PSRRVPEVNQQGEIREMEHPAHILAYYSLA
                541                                                        600

*    *   *  *   *
SEQ ID NO:18    GRRTDCPPSVTLLYPAF----
SEQ ID NO:22    GQRSDFPDTVVPLDTATCVDT
SEQ ID NO:20    GKRSDCPRSVVPLYPA-----
SEQ ID NO:37    GQRTDCPTTVRVLKEPI----
                601                621
```

Figure 2A

```
                                                                                             ***
SEQ ID NO:30    MPVMAPTASL---LLSPRPLPASRRVPSLPA-------LSASGRLRLRRARADTRLRVA
SEQ ID NO:32    MALPHSISALATTLTLSSPITKPHKVNPFPFSSNRNSQFLTKQTRPRSRRNLSLTPARVA
SEQ ID NO:36    ------------------------------------------------------LRVA
SEQ ID NO:38    MRATIPALSL---LVTPR--------LPSLAV-------PLAGGRLR-EGGRSRTRLRVA
                1                                                          60

**  *             ******************* ***   *********** *
SEQ ID NO:30    APPSVPGEAD--QAPGETEPSTSSAD---EKFVWRDHWYPVSLVEDLDPSVPTPFQLLNR
SEQ ID NO:32    APPSTVEADRLYPEAENNETEEEFSDESSSKFTWRDHWYPVSLIEDLNPLLPTPFQLLGR
SEQ ID NO:36    APTSVPGEAE--RAEEPSTSTSPESSGEKFVWRDHWYPVSLVEDLDPRVPTPFQLLNR
SEQ ID NO:38    APTSVPGEAA--EQAEPSTSAPES---GEKFSWRDHWYPVSLVEDLDPSRPTPFQLLNR
                61                                                         120

*    ****   *    *** ***************** **** * ****  *
SEQ ID NO:30    DLVIWKDPKSGEWVALDDRCPHRLAPLSEGRIDETGCLQCSYHGWSFDGSGACTRIPQAA
SEQ ID NO:32    EIVLWYDKSISQWVAFDDKCPHRLAPLSEGRIDEDGKLQCSYHGWSFDGCGSCVKIPQAS
SEQ ID NO:36    DLVIWNDPNSGDWVALDDRCPHRLAPLSEGRIDETGGLQCSYHGWSFDGSGACTRIPQAA
SEQ ID NO:38    DLVIWKEPKSGEWVALDDRCPHRLAPLSEGRIDETGCLQCSYHGWSFDGSGACTKIPQAM
                121                                                        180

******  *  ***  ****   ********* **** ******* *** ********
SEQ ID NO:30    PEGPEAKAVRSPKACAIKFPTLVSQGLLFVWPDENGWEKATATKPPMLPKEFEDPAFSTV
SEQ ID NO:32    SEGPEARAIGSPKACATRFPTLVSQGLLFVWADENGWEKAKASNPPMFPDDFDKPEFPTV
SEQ ID NO:36    PEGPEARAVRSPRACAIKFPTLLSQGLLFVWPDENGWDKAKATKPPMLPKEFDDPAFSTV
SEQ ID NO:38    PEGPEARAVRSPKACAIKFPTLVSQGLLFVWPDENGWEKAAATKPPMLPKEFEDPAFSTV
                181                                                        240
```

Figure 2B

```
                   ************************************** * ** *** **
SEQ ID NO:30       TIQRDLYYGYDTLMENVSDPSHIEFAXHKVTGRRDRARPLPFKMESSGAWGYSGSNSGNP
SEQ ID NO:32       NIQRDLFYGYDTLMENVSDPSHIEFAHHKVTGRRDRAKPLPFKMDSRGSWGFSGANEGNP
SEQ ID NO:36       TIQRDLFYGYDTLMENVSDPSHIEFAHHKVTGRRDRAKPLPFKMESSGAWGYSGANTGNP
SEQ ID NO:38       TIQRDLFYGYDTLMENVSDPSHIEFAHHKVTGRRDRARPLTFRMESSGAWGYSGANSGNP
                   241                                                        300

* ****   ************* ***** *************** ************
SEQ ID NO:30       RISATFVAPCYALNKIEIDTKLPIFGDQKWVIWICSFNIPMAPGKTRSIVCSARNFFQFS
SEQ ID NO:32       QISAKFVAPCYMMNKIEIDTKLPLPVVGDQKWVVWICSFNVPMAPGKTRSIVCSARNFFQFS
SEQ ID NO:36       RITATFEAPCYALNKIEIDTKLPIVGDQKWVIWICSFNIPMAPGKTRSIVCSARNFFQFT
SEQ ID NO:38       RITATFEAPCYALNKIEIDTKLPIFGDQKWVIWICSFNIPMAPGKTRSIVCSARNFFQFT
                   301                                                        360

** *****                              ************ * *
SEQ ID NO:30       MPGKAWWQL---------------------------VPRWYEHWTSNLVYDGDMIVLQGQEKIFLSAS
SEQ ID NO:32       VPGPAWWQVNVILLFAFNFKQCIHVTQVVPRWYEHWTSNLVYDGDMIVLQGQEKIFLSET
SEQ ID NO:36       MPGKAWWQF---------------------------VPRWYEHWTSNLVYDGDMIVLQGQEKVFLSAS
SEQ ID NO:38       MPGKAWWQL---------------------------VPRWYEHWTSNLVYDGDMIVLQGQEKIFLAAT
                   361                                                        420

* *  * ****    ************* ***************** *********
SEQ ID NO:30       KESSADINQQYTKITFTPTQADRFVLAFRAWLRKFGNSQPDWFGNPSQEVLPSTVLSKRE
SEQ ID NO:32       KEGG-DINKQYTNITFTPTQADRFVLAFRNWLRRHGNGQPEWFGNSSDQPLPSTVLSKRQ
SEQ ID NO:36       KESSADVNQQYTKLTFTPTQADRFVLAFRAWLRKFGNSQPDWYGSPSQDALPSTVLSKRE
SEQ ID NO:38       KESSTDINQQYTKITFTPTQADRFVLACRTWLRKFGNSQPEWFGNPTQEALPSTVLSKRE
                   421                                                        480
```

Figure 2C

```
                   ****  **  ******   *   *   **   ***  ****
SEQ ID NO:30       MLDRYEQHTLKCSSCKGAYNAFQTLQKVFMGATVA------------VLLLL-----
SEQ ID NO:32       MLDRFEQHTLKCSSCKAAYEGFQTWQKVLIGATVVFCATSGIPSDFQLRVLLAGLAVSA
SEQ ID NO:36       MLDRYEQHTLKCSSCRGAHKAFQTLQKVFMGATVVFGATSGIPADVQLRILLGAGALVSA
SEQ ID NO:38       MLDRYEQLSLKCSSCKGAYNAFQNLQKVFMGATVVCCAAAGIPPDVQLRLLIGAAALVSA
                   481                                                      540

SEQ ID NO:30       ------------AIAFALNQLQKNFEFVDYVHAEID
SEQ ID NO:32       ALAYVFYDRQKHFVFVDYVHADID
SEQ ID NO:36       AIAYAFHELQKNFVFVDYVHADID
SEQ ID NO:38       AIAYAFHELQKNFVFVDYVHADID
                   541                              564
```

DISEASE RESISTANCE FACTORS

This application is a continuation of U.S. patent application Ser. No. 10/009,791 filed Nov. 5, 2001, now abandoned, which is a national stage entry of PCT/US00/11956 filed May 3, 2000, which claims the benefit of U.S. Provisional Application No. 60/133,041, filed May 7, 1999.

FIELD OF THE INVENTION

This invention is in the field of plant molecular biology. More specifically, this invention pertains to nucleic acid fragments encoding disease resistance factors in plants and seeds.

BACKGROUND OF THE INVENTION

Plants synthesize signaling molecules in response to wounding, herbivore attack and pathogen attack. These compounds are derived from linoleic acid and stimulate the expression of several genes referred to as jasmonate-induced proteins. These include proteinase inhibitors, thionins, vegetative storage proteins, lipoxygenases, ribosome-inactivating proteins, enzymes of phenylpropanoid metabolism, and others. The jasmonates can also repress the expression of genes related to photosynthesis at the transcriptional and translational levels.

Coronatine is a phytotoxin produced by several pathovars of *Pseudomonas syringae* which induces leaf chlorosis, inhibits root growth and is thought to play a role in disease development by suppressing the disease-resistance genes and mimicking the action of methyl jasmonate. The COI1 protein contains an F-box-like motif and leucine-rich repeats. This protein may recruit regulators of defense response and pollen development for modification by ubiquitination (Xie et al., "COI1: An *Arabidopsis* Gene Required for Jasmonate-Regulated Defense and Fertility", (1998) *Science* 280: 1091-1094).

The maize Lls1 (lethal leaf spot1) locus is characterized by the initiation of necrotic lesions which expand to kill leaf-cells autonomously. The Lls1 gene is required to limit the spread of cell death in mature leaves. The Lls1-encoded protein (LLS1) contains two consensus binding motifs of aromatic ring-hydroxylating dioxygenases and may function to degrade a phenolic mediator of cell death. The LLS1 protein is expressed predominantly in the leaf epidermal tissue (Simmons et al. (1998) *Mol. Plant Microbe Interact.* 11:1110-1118; Gray et al. (1997) *Cell* 89:25-31).

The sequences encoding COI1 from corn, rice, soybean and wheat have yet to be determined as are the sequences encoding rice, soybean and wheat LLS1. Manipulation of the COI1 or LLS1 genes will be useful in engineering broad spectrum disease, insect and stress resistance. The genes encoding LLS1 will also be useful for herbicide discovery and design.

SUMMARY OF THE INVENTION

The present invention concerns an isolated polynucleotide comprising a nucleotide sequence selected from the group consisting of: (a) a first nucleotide sequence encoding a polypeptide of at least 60 amino acids selected from the group consisting of SEQ ID NOs:2, 4, 6, 8, 10, 12, 14, 16, 18, 20, 22, 24, 26, 28, 30, 32, 34, and 36; or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs:1, 3, 5, 7, 9, 11, 13, 15, 17, 19, 21, 23, 25, 27, 29, 31, 33, and 35.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, and 35 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a COI1 or an LLS1 protein of at least 60 amino acids comprising a polypeptide selected from the group consisting of SEQ ID NOs:2, 4, 6, 8, 10, 12, 14, 16, 18, 20, 22, 24, 26, 28, 30, 32, 34, and 36.

In an eighth embodiment, the invention relates to a method of selecting an isolated polynucleotide that affects the level of expression of a COI1 or an LLS1 protein or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the COI1 or the LLS1 protein or enzyme activity in the host cell containing the isolated polynucleotide; and (d) comparing the level of the COI1 or the LLS1 protein or enzyme activity in the host cell containing the isolated polynucleotide with the level of the COI1 or the LLS1 protein or enzyme activity in the host cell that does not contain the isolated polynucleotide.

In a ninth embodiment, the invention concerns a method of obtaining a nucleic acid fragment encoding a substantial portion of a COI1 or an LLS1 protein, preferably a plant COI1 or LLS1 protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, and 35, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a COI1 or an LLS1 protein amino acid sequence.

In a tenth embodiment, this invention relates to a method of obtaining a nucleic acid fragment encoding all or a substantial portion of the amino acid sequence encoding a COI1 or an LLS1 protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide or an isolated polypeptide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the COI1 or the LLS1 protein polynucleotide in an amount sufficient to complement a null mutant to provide a positive selection means.

In a thirteenth embodiment, this invention relates to a method of altering the level of expression of a disease resistance factor in a host cell comprising: (a) transforming a host cell with a chimeric gene of the present invention; and (b) growing the transformed host cell under conditions that are suitable for expression of the chimeric gene wherein expression of the chimeric gene results in production of altered levels of the disease resistance factor in the transformed host cell.

A further embodiment of the instant invention is a method for evaluating at least one compound for its ability to inhibit the activity of an LLS1 protein, the method comprising the steps of: (a) transforming a host cell with a chimeric gene comprising a nucleic acid fragment encoding an LLS1 polypeptide, operably linked to at least one suitable regulatory sequence; (b) growing the transformed host cell under conditions that are suitable for expression of the chimeric gene wherein expression of the chimeric gene results in production of LLS1 protein in the transformed host cell; (c) optionally purifying the LLS1 protein expressed by the transformed host cell; (d) treating the LLS1 protein with a compound to be tested; and (e) comparing the activity of the LLS1 protein that has been treated with a test compound to the activity of an untreated LLS1 protein, thereby selecting compounds with potential for inhibitory activity.

BRIEF DESCRIPTION OF THE DRAWINGS AND SEQUENCE LISTING

The invention can be more fully understood from the following detailed description, the accompanying drawings and the Sequence Listing which form a part of this application.

FIGS. 1A, 1B and 1C present an alignment of the amino acid sequences derived from corn clone p0128.cpici34r:fis (SEQ ID NO:18), rice clone r10n.pk099.p14:fis (SEQ ID NO:20), and soybean clone sgs4c.pk003.k23:fis (SEQ ID NO:22) with the *Arabidopsis thaliana* COI1 sequence (NCBI General Identifier No.3158394; SEQ ID NO:37). Underlined amino acids in SEQ ID NO:37 correspond to the degenerate F-box motif and the 16 imperfect leucine-rich repeats (LRRs) indicated by Xie et al. (1998, *Science* 280:1091-1094). Amino acids conserved among all the species are indicated by an Asterisk (*) above the alignment. Dashes are used by the program to maximize the alignment.

FIGS. 2A, 2B and 2C present an alignment of the amino acid sequences derived from rice clone rds2c.pk005.b12:fis (SEQ ID NO:30), soybean clone sgc2c.pk001.c22:fis (SEQ ID NO:32), and wheat clone wlmk1.pk0015.h3:fis (SEQ ID NO:36) with the *Zea mays* LLS1 sequence (NCBI General Identifier Nos. 7489721, SEQ ID NO:38). Underlined amino acids in SEQ ID NO:38 correspond to consensus sequence for coordinating the Reiske-type [2Fe-2S] cluster and the mononuclear non-heme binding site (Gray et al. (1997) *Cell* 89:25-31). Amino acids conserved among all sequences are indicated by an Asterisk (*) above the alignment. Dashes are used by the program to maximize the alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Disease Resistance Factors

| Protein | Clone Designation | SEQ ID NO: (Nucleotide) | SEQ ID NO: (Amino Acid) |
|---|---|---|---|
| Corn COI1 | p0128.cpici34r | 1 | 2 |
| Rice COI1 | Contig of: rlr2.pk0027.h4 r10n.pk099.p14 r10n.pk0047.c5 | 3 | 4 |
| Soybean COI1 | sgs4c.pk003.k23 | 5 | 6 |
| Wheat COI1 | Contig of: wre1n.pk0122.d3 wl1n.pk0018.f8 | 7 | 8 |
| Rice LLS1 | rds2c.pk005.b12 | 9 | 10 |
| Soybean LLS1 | sgc2c.pk001.c22 | 11 | 12 |
| Wheat LLS1 | wlmk1.pk0015.h3 | 13 | 14 |
| Corn COI1 | p0037.crwbs69r | 15 | 16 |
| Corn COI1 | p0128.cpici34r:fis | 17 | 18 |
| Rice COI1 | r10n.pk099.p14:fis | 19 | 20 |
| Soybean COI1 | sgs4c.pk003.k23:fis | 21 | 22 |
| Wheat COI1 | wl1n.pk0049.f7 | 23 | 24 |
| Wheat COI1 | wlm0.pk0009.d7 | 25 | 26 |
| Wheat COI1 | wre1n.pk0122.d3:fis | 27 | 28 |
| Rice LLS1 | rds2c.pk005.b12:fis | 29 | 30 |
| Soybean LLS1 | sgc2c.pk001.c22:fis | 31 | 32 |
| Wheat LLS1 | wlm0.pk0002.c10 | 33 | 34 |
| Wheat LLS1 | wlmk1.pk0015.h3:fis | 35 | 36 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs: 1, 3, 5, 7, 9, 11, 13, 15, 17, 19, 21, 23, 25, 27, 29, 31, 33, and 35, or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, and 35, and the complement of such nucleotide sequences may be used in methods of selecting an isolated polynucleotide that affects the expression of a COI1 or an LLS1 protein in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level, of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including, regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

"3' Non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to the translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refer to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell.. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 60 amino acids selected from the group consisting of SEQ ID NOs:2, 4, 6, 8, 10, 12, 14, 16, 18, 20, 22, 24, 26, 28, 30, 32, 34, and 36, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9, 11, 13, 15, 17, 19, 21, 23, 25, 27, 29, 31, 33, and 35.

Nucleic acid fragments encoding at least a substantial portion of several disease resistance factors have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the; same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other COI1 or LLS1 proteins, either as cDNAs or genomic DNAs, could be isolated directly by using all or a substantial portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, and 35 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a COI1 or an LLS1 protein, preferably a substantial portion of a plant COI1 or LLS1 protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, and 35, and the complement of such nucleotide sequences; and amplifying a nucleic acid fragment (preferably a cDNA inserted in a cloning vector) using the oligonucleotide primer. The amplified nucleic acid fragment preferably will encode a portion of a COI1 or an LLS1 protein.

Availability of the instant nucleotide and deduced amino acid sequences facilitates immunological screening of cDNA expression libraries. Synthetic peptides representing substantial portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of disease resistance in those cells. LLS1 is a suppressor of cell death, thus decreasing its production will result in cell death. Overexpression of COI1 should induce systemic resistance to a broad range of pathogens.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

In another embodiment, the present invention concerns a polypeptide of at least 60 amino acids selected from the group consisting of SEQ ID NOs:2, 4, 6, 8, 10, 12, 14, 16, 18, 20, 22, 24, 26, 28, 30, 32, 34, and 36.

The instant polypeptides (or substantial portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded disease resistance factor. An example of a vector for high level expression of the instant polypeptides in a bacterial host is provided (Example 7).

Additionally, the instant LLS1 protein can be used as a target to facilitate design and/or identification of inhibitors of those enzymes that may be useful as herbicides. This is desirable because the LLS1 described herein catalyzes inactivation of the cell-death signal. Accordingly, inhibition of the activity of LLS1 could lead to inhibition plant growth. Thus, the instant LLS1 could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in sits hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| p0037 | Corn V5 Stage* Roots Infested With Corn Root Worm | p0037.crwbs69r |
| p0128 | Corn Primary and Secondary Immature Ear, Pooled | p0128.cpici34r |
| rds2c | Rice Developing Seeds From Middle of the Plant | rds2c.pk005.b12 |
| rl0n | Rice 15 Day Old Leaf** | rl0n.pk0047.c5 |
| rl0n | Rice 15 Day Old Leaf** | rl0n.pk099.p14 |
| rlr2 | Rice Leaf 15 Days After Germination, 2 Hours After Infection of Strain *Magaporthe grisea* 4360-R-62 (AVR2-YAMO); Resistant | rlr2.pk0027.h4 |
| sgc2c | Soybean Cotyledon 12–20 Days After Germination (Mature Green) | sgc2c.pk001.c22 |
| sgs4c | Soybean Seeds 2 Days After Germination | sgs4c.pk003.k23 |
| wl1n | Wheat Leaf From 7 Day Old Seedling** | wl1n.pk0018.f8 |
| wl1n | Wheat Leaf From 7 Day Old Seedling** | wl1n.pk0049.f7 |
| wlm0 | Wheat Seedlings 0 Hour After Inoculation With *Erysiphe graminis* f. sp *tritici* | wlm0.pk0002.c10 |
| wlm0 | Wheat Seedlings 0 Hour After Inoculation With *Erysiphe graminis* f. sp *tritici* | wlm0.pk0009.d7 |
| wlmk1 | Wheat Seedlings 1 Hour After Inoculation With *Erysiphe graminis* f. sp *tritici* and Treatment With Herbicide*** | wlmk1.pk0015.h3 |
| wre1n | Wheat Root From 7 Day Old Etiolated Seedling** | wre1n.pk0122.d3 |

*Corn developmental stages are explained in the publication "How a corn plant develops" from the Iowa State University Coop. Ext. Service Special Report No. 48 reprinted June 1993.
**These libraries were normalized essentially as described in U.S. Pat. No. 5,482,845, incorporated herein by reference.
***Application of 6-iodo-2-propoxy-3-propyl-4(3H)-quinazolinone; synthesis and methods of using this compound are described in U.S. Pat. No. 5,747,497, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651-1656). The resulting ESTs are analyzed using a Perkin Elmer Model 377 fluorescent sequencer.

Example 2

Identification of cDNA Clones cDNA clones encoding disease resistance factors were identified by conducting BLAST (Basic Local Alignment Search Tool; Altschul et al. (1993) J. Mol. Biol. 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) Nat. Genet. 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding COI1

The BLASTX search using the EST sequences from clones listed in Table 3 revealed similarity of the polypeptides encoded by the Contig to an unknown protein from chromosome 2 of Arabidopsis thaliana (NCBI General Identifier No. 2088647) which is identical to the polypeptides encoded by the cDNA to COI1 protein from Arabidopsis thaliana (NCBI General Identifier No. 3158394). Shown in Table 3 are the BLAST results for individual ESTs ("EST"), or for the sequences of contigs assembled from two or more ESTs ("Contig"):

TABLE 3

BLAST Results for Clones Encoding Polypeptides Homologous to COI1

| Clone | Status | BLAST pLog Score 2088647 or 3158394 |
|---|---|---|
| p0128.cpici34r | EST | 42.30 |
| Contig of: | Contig | 104.00 |
| rlr2.pk0027.h4 | | |
| rl0n.pk099.p14 | | |
| rl0n.pk0047.c5 | | |
| sgs4c.pk003.k23 | EST | 48.00 |
| Contig of: | Contig | 76.00 |
| wre1n.pk0122.d3 | | |
| wl1n.pk0018.f8 | | |

Further sequencing allowed the determination of the sequence of the entire cDNA insert in clones p0128.cpici34r, rl0n.pk099.p14, sgs4c.pk003.k23, and wre1n.pk0122.d3. Further searching of the DuPont proprietary database allowed the identification of other corn and wheat ESTs with similarities to COI1. The BLASTX search using the EST sequences or the BLASTP search using the amino acid sequences encoded by the entire cDNA inserts from clones listed in Table 3 revealed similarity of the polypeptides encoded by the Contig to an unknown protein from chromosome 2 of Arabidopsis thaliana (NCBI General Identifier No. 2088647) which is identical to the polypeptides encoded by the cDNA to COI1 protein from Arabidopsis thaliana (NCBI General Identifier No. 3158394). Shown in Table 4 are the BLAST results for individual ESTs ("EST"), for the amino acid sequences derived from the sequences of the entire cDNA inserts comprising the indicated cDNA clones ("FIS"), or from the amino acid sequences of the entire polypeptide derived from an FIS or an FIS and PCR ("CGS"):

TABLE 4

BLAST Results for Sequences Encoding Polypeptides Homologous to COI1

| Clone | Status | BLAST pLog Score 2088647 or 3158394 |
|---|---|---|
| p0037.crwbs69r | EST | 38.00 |
| p0128.cpici34r:fis | FIS | 135.00 |
| rl0n.pk099.p14:fis | CGS | >254.00 |
| sgs4c.pk003.k23:fis | CGS | >254.00 |
| wl1n.pk0049.f7 | EST | 7.00 |
| wlm0.pk0009.d7 | EST | 15.40 |
| wre1n.pk0122.d3:fis | FIS | 75.70 |

FIGS. 1A, 1B and 1C present an alignment of the amino acid sequences set forth in SEQ ID NOs:18, 20, and 22 and the Arabidopsis thaliana sequence (NCBI General Identifier No. 3158394; SEQ ID NO:37). Underlined amino acids in SEQ ID NO:37 correspond to the degenerate F-box motif and the 16 imperfect leucine-rich repeats (LRRs) indicated by Xie et al. (1998, Science 280:1091-1094). The data in Table 5 presents a calculation of the percent identity of the amino acid sequences set forth in SEQ ID NOs:2, 4, 6, 8, 16, 18, 20, 22, 24, 26, and 28 and the Arabidopsis thaliana COI1 protein sequence (SEQ ID NO:37).

TABLE 5

Percent Identity of Amino Acid Sequences Deduced From the Nucleotide Sequences of cDNA Clones Encoding Polypeptides Homologous to COI1

| SEQ ID NO. | Percent Identity to 2088647 (SEQ ID NO: 37) |
|---|---|
| 2 | 42.3 |
| 4 | 68.2 |
| 6 | 74.1 |
| 8 | 67.2 |
| 16 | 39.2 |
| 18 | 52.0 |
| 20 | 55.4 |
| 22 | 67.7 |
| 24 | 28.9 |
| 26 | 29.9 |
| 28 | 69.4 |

Sequence alignments and percent identity calculations were performed using the Megalign program of the LASER-GENE bioinformatics computing suite (DNASTAR Inc.. Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW-5 and DIAGONALS SAVED=5. Sequence alignments, BLAST scores and probabilities indicate that the nucleic acid fragments comprising the instant cDNA clones encode substantial portions of a corn, a rice, a soybean, and a wheat COI1 protein and the entire rice and soybean COI1 proteins.

Example 4

Characterization of cDNA Clones Encoding LLS1

The BLASTX search using the EST sequences from clones listed in Table 6 revealed similarity of the polypeptides encoded by the cDNAs to LLS1 from *Zea mays* (NCBI General Identifier No. 1935912) and by the contig to LLS1 from *Arabidopsis thaliana* (NCBI General Identifier No. 1935914). Shown in Table 6 are the organisms from which the closest art sequence is derived from, the NCBI General Identifier Number, and BLAST results for individual ESTs ("EST"):

TABLE 6

BLAST Results for Clones Encoding Polypeptides Homologous to LLS1

| Clone | Status | Organism | NCBI gi No. | BLAST pLog Score |
|---|---|---|---|---|
| rds2c.pk005.b12 | EST | Zea mays | 1935912 | 53.30 |
| sgc2c.pk001.c22 | EST | Arabidopsis thaliana | 1935914 | 28.30 |
| wlmk1.pk0015.h3 | EST | Zea mays | 1935912 | 68.70 |

The sequence of the entire cDNA insert from the clones listed in Table 6 was determined. Further searching of the DuPont proprietary database allowed the identification of another, more 5'. LLS1 -encoding wheat clone. The BLASTX search using the EST sequences or the BLASTP search using the amino acid sequences encoded by the entire cDNA inserts from clones listed in Table 6 revealed similarity of the polypeptides encoded by the cDNAs to LLS1 from *Zea mays* (NCBI General Identifier Nos. 1935912 and 7489721) and by the contig to LLS1 from *Arabidopsis thaliana* (NCBI General Identifier No.1935914). The two *Zea mays* amino acid sequences are identical through 505 amino acids. The amino acid sequence having NCBI General Identifier No. 7489721 contains 15 extra amino acids at the C-terminus compared to the amino acid sequence presented in NCBI General Identifier No.1935912. Shown in Table 7 are the organisms from which the closest art sequence is derived from, the NCBI General Identifier Number, and the BLAST results for individual ESTs ("EST"), for the amino acid sequences derived from the sequences of the entire cDNA inserts comprising the indicated cDNA clones ("FIS"), or for the amino acid sequences of the entire polypeptide derived from an FIS or an FIS and PCR ("CGS"):

TABLE 7

BLAST Results for Sequences Encoding Polypeptides Homologous to LLS1

| Clone | Status | Organism | NCBI gi No. | BLAST pLog Score |
|---|---|---|---|---|
| rds2c.pk005.b12:fis | FIS | Zea mays | 1935912 | >254.00 |
| sgc2c.pk001.c22:fis | CGS | Arabidopsis thaliana | 1935914 | >254.00 |
| wlm0.pk0002.c10 | EST | Zea mays | 1935912 | 7.00 |
| wlmk1.pk0015.h3:fis | FIS | Zea mays | 7489721 | >254.00 |

FIGS. 2A, 2B and 2C present an alignment of the amino acid sequences set forth in SEQ ID NOs:30, 32, and 36 and the *Zea mays* sequence (NCBI General Identifier Nos. 7489721, SEQ ID NO:38). Underlined amino acids in SEQ ID NO:38 correspond to the consensus sequence for coordinating the Reiske-type [2Fe-2S] cluster and the mononuclear non-heme binding site (Gray et al. (1997) *Cell* 89:25-31) The data in Table 8 presents a calculation of the percent identity of the amino acid sequences set forth in SEQ ID NOs:10, 12, 14, 30, 32, and 36 and the *Zea mays* sequence (SEQ ID NO:38).

TABLE 8

Percent Identity of Amino Acid Sequences Deduced From the Nucleotide Sequences of cDNA Clones Encoding Polypeptides Homologous to LLS1

| SEQ ID NO. | Percent Identity to 7489721 (SEQ ID NO: 38) |
|---|---|
| 10 | 79.4 |
| 12 | 65.2 |
| 14 | 86.7 |
| 30 | 83.1 |
| 32 | 67.9 |
| 34 | 22.9 |
| 36 | 85.8 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10 GAP LENGTH PENALTY=10). Default parameters for pairwise alignments using the Clustal method were KTUPLE 1, GAP PENALTY=3, WINDOW=5 and DIAGONALS SAVED=5.

Sequence alignments, BLAST scores and probabilities indicate that the nucleic acid fragments comprising the instant cDNA clones encode a substantial portion and an entire soybean an rice LLS1 proteins and two portions and a substantial portion wheat LLS1 protein.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of mercury. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2.4-D. After two weeks the tissue can be transferred to regeneration medium (Fromm et al. (1990) *Bio/Technology* 8:833-839).

Example 6

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al.(1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of LLS1

The LLS1 polypeptide described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant LLS1 polypeptide may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin. enterokinase and factor Xa. However, any protease can be used which specifically cleaves the peptide connecting the fusion protein and the enzyme.

Purification of the instant LLS1 polypeptide, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant LLS1 polypeptide are expressed as fusion proteins, the purification protocol may include the use of an affinity resin which is specific for the fusion protein tag attached to the expressed enzyme or an affinity resin containing ligands which are specific for the enzyme. For example, the instant LLS1 polypeptide may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant LLS1 polypeptide disclosed herein. Assays may be conducted under well known experimental conditions which permit optimal enzymatic activity. For example, assays for LLS1 are presented by Gray et al. (1997) *Cell* 89:25-31.

What is claimed is:

1. An isolated polynucleotide comprising:
   (a) a nucleotide sequence encoding a COI1 polypeptide useful for disease resistance, wherein the polypeptide has an amino acid sequence of at least 90% sequence identity, based on the Clustal method of alignment, when compared to SEQ ID NO:22, or
   (b) the full-length complement of the nucleotide sequence of (a).

2. The polynucleotide of claim 1, wherein the amino acid sequence of the polypeptide has at least 95% sequence identity, based on the Clustal method of alignment, when compared to SEQ ID NO:22.

3. The polynucleotide of claim 1, wherein the amino acid sequence of the polypeptide comprises SEQ ID NO:22.

4. The polynucleotide of claim 1, wherein the nucleotide sequence comprises SEQ ID NO:21.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A plant comprising the recombinant DNA construct of claim 6.

10. A seed comprising the recombinant DNA construct of claim 6.

* * * * *

SEQUENCE LISTING

```
<160> NUMBER OF SEQ ID NOS: 38

<210> SEQ ID NO 1
<211> LENGTH: 701
<212> TYPE: DNA
<213> ORGANISM: Zea mays
<220> FEATURE:
<221> NAME/KEY: unsure
<222> LOCATION: (389)
<223> OTHER INFORMATION: n = A, T, C, or G
<220> FEATURE:
<221> NAME/KEY: unsure
<222> LOCATION: (457)
<223> OTHER INFORMATION: n = A, T, C, or G
<220> FEATURE:
<221> NAME/KEY: unsure
<222> LOCATION: (531)
<223> OTHER INFORMATION: n = A, T, C, or G
<220> FEATURE:
<221> NAME/KEY: unsure
<222> LOCATION: (591)
<223> OTHER INFORMATION: n = A, T, C, or G
<220> FEATURE:
<221> NAME/KEY: unsure
```

```
<222> LOCATION: (637)
<223> OTHER INFORMATION: n = A, T, C, or G
<220> FEATURE:
<221> NAME/KEY: unsure
<222> LOCATION: (658)
<223> OTHER INFORMATION: n = A, T, C, or G
<220> FEATURE:
<221> NAME/KEY: unsure
<222> LOCATION: (693)
<223> OTHER INFORMATION: n = A, T, C, or G
<220> FEATURE:
<221> NAME/KEY: unsure
<222> LOCATION: (699)..(700)
<223> OTHER INFORMATION: n = A, T, C, or G

<400> SEQUENCE: 1
gcggacgcgt gggctggaaa cactttcct ggaagaaagc acaattgatg agaaagaaaa      60
tgatgagtgg atccgtgagc ttgctacgag caattctgtt cttgagacac tgaatttctt    120
tctaacagat ctcagggcat ccccagagta tcttaccctc cttgtgcgca actgtcaacg    180
attgaaaact ctgaagatta gtgaatgttt catgcccgat ctggtcagtt tgttccgaac    240
tgcacaaaca ctacaagagt tcgctggtgg ttcctttgaa gagcagggtc aacctgtggc    300
aagtagaaat tatgagaact actattttcc tccttcactg caccgcttga gtttgctcta    360
catgggaaca aatgatatgc aaatactgnt tccatatgct actgcactta agaagttaga    420
ccttcagttt acattccttt ccacagagga tcattgncag atagttcaac gctgctccaa    480
tctggaaacc ttagaggtga gggatgtcat aggggatcgg ggactacaag ntggtgcaca    540
gacctgcaag aaattgcata ggctcagagt agagagagga gatgatgatc nagaggtctt    600
gaggatgaac caaggtagga atttcacagg gtggggntga tgggtatagg cccaaggntg    660
gccttgggtt gacatactgg gccgatacca tgnattagnn c                         701

<210> SEQ ID NO 2
<211> LENGTH: 194
<212> TYPE: PRT
<213> ORGANISM: Zea mays
<220> FEATURE:
<221> NAME/KEY: UNSURE
<222> LOCATION: (128)
<223> OTHER INFORMATION: Xaa = any amino acid
<220> FEATURE:
<221> NAME/KEY: UNSURE
<222> LOCATION: (150)
<223> OTHER INFORMATION: Xaa = any amino acid
<220> FEATURE:
<221> NAME/KEY: UNSURE
<222> LOCATION: (175)
<223> OTHER INFORMATION: Xaa = any amino acid

<400> SEQUENCE: 2

Arg Gly Leu Glu Thr Leu Phe Leu Glu Glu Ser Thr Ile Asp Glu Lys
 1               5                  10                  15

Glu Asn Asp Glu Trp Ile Arg Glu Leu Ala Thr Ser Asn Ser Val Leu
            20                  25                  30

Glu Thr Leu Asn Phe Phe Leu Thr Asp Leu Arg Ala Ser Pro Glu Tyr
        35                  40                  45

Leu Thr Leu Leu Val Arg Asn Cys Gln Arg Leu Lys Thr Leu Lys Ile
    50                  55                  60

Ser Glu Cys Phe Met Pro Asp Leu Val Ser Leu Phe Arg Thr Ala Gln
65                  70                  75                  80

Thr Leu Gln Glu Phe Ala Gly Gly Ser Phe Glu Glu Gln Gly Gln Pro
                85                  90                  95
```

```
Val Ala Ser Arg Asn Tyr Glu Asn Tyr Tyr Phe Pro Pro Ser Leu His
            100                 105                 110
Arg Leu Ser Leu Leu Tyr Met Gly Thr Asn Asp Met Gln Ile Leu Xaa
        115                 120                 125
Pro Tyr Ala Thr Ala Leu Lys Lys Leu Asp Leu Gln Phe Thr Phe Leu
    130                 135                 140
Ser Thr Glu Asp His Xaa Gln Ile Val Gln Arg Cys Ser Asn Leu Glu
145                 150                 155                 160
Thr Leu Glu Val Arg Asp Val Ile Gly Asp Arg Gly Leu Gln Xaa Gly
                165                 170                 175
Ala Gln Thr Cys Lys Lys Leu His Arg Leu Arg Val Glu Arg Gly Asp
            180                 185                 190
Asp Asp
```

<210> SEQ ID NO 3
<211> LENGTH: 844
<212> TYPE: DNA
<213> ORGANISM: Oryza sativa
<220> FEATURE:
<221> NAME/KEY: unsure
<222> LOCATION: (352)
<223> OTHER INFORMATION: n = A, T, C, or G
<220> FEATURE:
<221> NAME/KEY: unsure
<222> LOCATION: (823)
<223> OTHER INFORMATION: n = A, T, C, or G

<400> SEQUENCE: 3

```
atcactccaa cttactagtt cttgcggtga ggaatgtgat tggagataga ggattagggg     60
ttgttgcaga cacatgcaag aagctacaaa gactcagagt tgagcgagga gatgatgatc    120
caggtttgca agaagaacaa ggaggagtct ctcaagtcgg gttgacaact gtagccgtag    180
gatgccgtga actggaatac atagctgcct atgtgtctga tatcacaaat ggggccctgg    240
agtctattgg gactttctgc aaaaatcttt gcgacttccg tcttgtccta ctcgatagag    300
aagagaggat aacagatttg cccttagaca atggtgtccg tgcactgctg angggctgca    360
cgaaacttcg gaggtttgct ctatacttga gaccaggggg actttcagat acaggccttg    420
gctatattgg acagtacagt ggaattatcc aatacatgct tctgggtaat gttggggaaa    480
cagatgatgg tctgatccgg tttgcattgg ggtgtgagaa cctgcggaag cttgagctaa    540
ggagttgttg cttcagtgag caagctttag cccgcgctat acggagtatg ccttccctga    600
gatacgtgtg ggtacagggc tacaaggctt ctaagactgg tcacgatctc atgctcatgg    660
caggcccttc tggaacatag agtttacacc tcccagaaga ctggtcacga tctcatgctc    720
atggcaggcc cttctggaac atagagttta cacctcccag ttctgagaat gcaaatcgaa    780
tgagagaaga tggtgaacct tgtgtaatat caactcagat acnctgcgga cgtaatacga    840
tagg                                                                 844
```

<210> SEQ ID NO 4
<211> LENGTH: 236
<212> TYPE: PRT
<213> ORGANISM: Oryza sativa
<220> FEATURE:
<221> NAME/KEY: UNSURE
<222> LOCATION: (115)
<223> OTHER INFORMATION: Xaa = any amino acid

<400> SEQUENCE: 4

```
Asn Leu Leu Val Leu Ala Val Arg Asn Val Ile Gly Asp Arg Gly Leu
```

```
              1               5              10              15
Gly Val Val Ala Asp Thr Cys Lys Lys Leu Gln Arg Leu Arg Val Glu
                20                  25                  30
Arg Gly Asp Asp Asp Pro Gly Leu Gln Glu Glu Gln Gly Gly Val Ser
            35                  40                  45
Gln Val Gly Leu Thr Thr Val Ala Val Gly Cys Arg Glu Leu Glu Tyr
        50                  55                  60
Ile Ala Ala Tyr Val Ser Asp Ile Thr Asn Gly Ala Leu Glu Ser Ile
65                  70                  75                  80
Gly Thr Phe Cys Lys Asn Leu Cys Asp Phe Arg Leu Val Leu Leu Asp
                85                  90                  95
Arg Glu Glu Arg Ile Thr Asp Leu Pro Leu Asp Asn Gly Val Arg Ala
                100                 105                 110
Leu Leu Xaa Gly Cys Thr Lys Leu Arg Arg Phe Ala Leu Tyr Leu Arg
            115                 120                 125
Pro Gly Gly Leu Ser Asp Thr Gly Leu Gly Tyr Ile Gly Gln Tyr Ser
        130                 135                 140
Gly Ile Ile Gln Tyr Met Leu Leu Gly Asn Val Gly Glu Thr Asp Asp
145                 150                 155                 160
Gly Leu Ile Arg Phe Ala Leu Gly Cys Glu Asn Leu Arg Lys Leu Glu
                165                 170                 175
Leu Arg Ser Cys Cys Phe Ser Glu Gln Ala Leu Ala Arg Ala Ile Arg
                180                 185                 190
Ser Met Pro Ser Leu Arg Tyr Val Trp Val Gln Gly Tyr Lys Ala Ser
            195                 200                 205
Lys Thr Gly His Asp Leu Met Leu Met Ala Arg Pro Phe Trp Asn Ile
    210                 215                 220
Glu Phe Thr Pro Pro Arg Arg Leu Val Thr Ile Ser
225                 230                 235

<210> SEQ ID NO 5
<211> LENGTH: 482
<212> TYPE: DNA
<213> ORGANISM: Glycine max

<400> SEQUENCE: 5
gcggaagaca cgtgtggtcg acgtggtcct cgactgcgtc atcccttaca tcgacgaccc      60
caaggaccgc gacgccgttt cccaggtgtg tcgacgctgg tacgagctcg actcgctcac     120
ccgcaagcac gtcaccatcg cgctctgcta caccaccacc ccggctcgcc tccgccgccg     180
cttcccgcac ctcgagtcgc tcaagctcaa gggcaagccc cgagccgcaa tgttcaactt     240
gatacccgag gattggggcg acacgtcac tccctgggtc aaagagattt ctcaagtact     300
tcgattgcct caagagcctc cacttccgcc gcatgattgt caaggattc cgatcttcag     360 aatctcgctc gtgaccgcgg tcacgtgctt cacgctctca agcttgaca gtgctccgg     420 tttcaacaac gatggtcctt ccatatcgg gtcgcttttg caaagaagtt taagagtcct     480
gt                                                                   482

<210> SEQ ID NO 6
<211> LENGTH: 108
<212> TYPE: PRT
<213> ORGANISM: Glycine max
<220> FEATURE:
<221> NAME/KEY: UNSURE
<222> LOCATION: (97)
<223> OTHER INFORMATION: Xaa = any amino acid
```

-continued

```
<400> SEQUENCE: 6

Val Asp Val Val Leu Asp Cys Val Ile Pro Tyr Ile Asp Asp Pro Lys
1               5                   10                  15

Asp Arg Asp Ala Val Ser Gln Val Cys Arg Arg Trp Tyr Glu Leu Asp
            20                  25                  30

Ser Leu Thr Arg Lys His Val Thr Ile Ala Leu Cys Tyr Thr Thr Thr
        35                  40                  45

Pro Ala Arg Leu Arg Arg Arg Phe Pro His Leu Glu Ser Leu Lys Leu
    50                  55                  60

Lys Gly Lys Pro Arg Ala Ala Met Phe Asn Leu Ile Pro Glu Asp Trp
65                  70                  75                  80

Gly Gly His Val Thr Pro Trp Val Lys Glu Ile Ser Gln Val Leu Arg
                85                  90                  95

Xaa Leu Lys Ser Leu His Phe Arg Arg Met Ile Val
            100                 105

<210> SEQ ID NO 7
<211> LENGTH: 794
<212> TYPE: DNA
<213> ORGANISM: Triticum aestivum
<220> FEATURE:
<221> NAME/KEY: unsure
<222> LOCATION: (270)
<223> OTHER INFORMATION: n = A, T, C, or G
<220> FEATURE:
<221> NAME/KEY: unsure
<222> LOCATION: (356)
<223> OTHER INFORMATION: n = A, T, C, or G
<220> FEATURE:
<221> NAME/KEY: unsure
<222> LOCATION: (675)
<223> OTHER INFORMATION: n = A, T, C, or G
<220> FEATURE:
<221> NAME/KEY: unsure
<222> LOCATION: (689)
<223> OTHER INFORMATION: n = A, T, C, or G
<220> FEATURE:
<221> NAME/KEY: unsure
<222> LOCATION: (702)
<223> OTHER INFORMATION: n = A, T, C, or G
<220> FEATURE:
<221> NAME/KEY: unsure
<222> LOCATION: (729)
<223> OTHER INFORMATION: n = A, T, C, or G
<220> FEATURE:
<221> NAME/KEY: unsure
<222> LOCATION: (743)
<223> OTHER INFORMATION: n = A, T, C, or G
<220> FEATURE:
<221> NAME/KEY: unsure
<222> LOCATION: (752)
<223> OTHER INFORMATION: n = A, T, C, or G
<220> FEATURE:
<221> NAME/KEY: unsure
<222> LOCATION: (761)
<223> OTHER INFORMATION: n = A, T, C, or G
<220> FEATURE:
<221> NAME/KEY: unsure
<222> LOCATION: (769)
<223> OTHER INFORMATION: n = A, T, C, or G
<220> FEATURE:
<221> NAME/KEY: unsure
<222> LOCATION: (777)
<223> OTHER INFORMATION: n = A, T, C, or G
<220> FEATURE:
<221> NAME/KEY: unsure
<222> LOCATION: (783)
<223> OTHER INFORMATION: n = A, T, C, or G
<220> FEATURE:
<221> NAME/KEY: unsure
```

<222> LOCATION: (785)
<223> OTHER INFORMATION: n = A, T, C, or G
<220> FEATURE:
<221> NAME/KEY: unsure
<222> LOCATION: (790)
<223> OTHER INFORMATION: n = A, T, C, or G
<220> FEATURE:
<221> NAME/KEY: unsure
<222> LOCATION: (793)
<223> OTHER INFORMATION: n = A, T, C, or G

<400> SEQUENCE: 7

```
gtaggattga tggctgtagc tgaaggctgt cctgatttgg agtactgggc agtacatgtg      60
tctgacatta caaatgcagc tcttgaggct attggcgcat tcagcaaaaa cctgaacgat     120
ttccgacttg tcctgcttga tagagaggtg catataactg aactgcccct tgacaacggg     180
gttcgggctt tgctgagagg ttgcaccaaa ctccggaggt ttgcatttta tgtgagacct     240
ggagctctat cagatattgg cctttcttan gttgggcgaa tttagcaaga ccgtccgcta     300
catgttgctt gggaatgccg ggggtctga tgatggactg ctggcatttg cacgangatg      360
cccaagcttg cagaaattgg agctaaggag ttgctgcttt agtgaacgtg cattggcagt     420
tgcagcctta cagctgaagt cactcagata tctttgggtg cagggataca aggcatctcc     480
tactggcacc gatctcatgg caatggtacg ccccttctgg aacattgagt ttattgcacc     540
aaatcaagat gagccttgcc cagagggtca ggacagattt ggcatactac tctctggtgg     600
ggaaggcaga ttgtcctagt cagtattccc tccatcgtag tgggagctaa aagaccacca     660
ccagtttact gacancatgt tgatgcagna accacatcgg anaggaattc actacagtgc     720
aattagggnt gaagctcagt aangaccatc tnatgcttga nttagggana tttgggnact     780
gtnantgcan agna                                                       794
```

<210> SEQ ID NO 8
<211> LENGTH: 177
<212> TYPE: PRT
<213> ORGANISM: Triticum aestivum
<220> FEATURE:
<221> NAME/KEY: UNSURE
<222> LOCATION: (89)
<223> OTHER INFORMATION: Xaa = any amino acid
<220> FEATURE:
<221> NAME/KEY: UNSURE
<222> LOCATION: (118)
<223> OTHER INFORMATION: Xaa = any amino acid

<400> SEQUENCE: 8

```
Gly Leu Met Ala Val Ala Glu Gly Cys Pro Asp Leu Glu Tyr Trp Ala
1               5                   10                  15
Val His Val Ser Asp Ile Thr Asn Ala Ala Leu Glu Ala Ile Gly Ala
            20                  25                  30
Phe Ser Lys Asn Leu Asn Asp Phe Arg Leu Val Leu Leu Asp Arg Glu
        35                  40                  45
Val His Ile Thr Glu Leu Pro Leu Asp Asn Gly Val Arg Ala Leu Leu
    50                  55                  60
Arg Gly Cys Thr Lys Leu Arg Arg Phe Ala Phe Tyr Val Arg Pro Gly
65                  70                  75                  80
Ala Leu Ser Asp Leu Ala Phe Leu Xaa Leu Gly Glu Phe Ser Lys Thr
                85                  90                  95
Val Arg Tyr Met Leu Leu Gly Asn Ala Gly Gly Ser Asp Asp Gly Leu
            100                 105                 110
Leu Ala Phe Ala Arg Xaa Cys Pro Ser Leu Gln Lys Leu Glu Leu Arg
```

```
                115                 120                 125
Ser Cys Cys Phe Ser Glu Arg Ala Leu Ala Val Ala Ala Leu Gln Leu
    130                 135                 140
Lys Ser Leu Arg Tyr Leu Trp Val Gln Gly Tyr Lys Ala Ser Pro Thr
145                 150                 155                 160
Gly Thr Asp Leu Met Ala Met Val Arg Pro Phe Trp Asn Ile Glu Phe
                165                 170                 175
Ile
```

<210> SEQ ID NO 9
<211> LENGTH: 426
<212> TYPE: DNA
<213> ORGANISM: Oryza sativa
<220> FEATURE:
<221> NAME/KEY: unsure
<222> LOCATION: (270)
<223> OTHER INFORMATION: n = A, T, C, or G
<220> FEATURE:
<221> NAME/KEY: unsure
<222> LOCATION: (380)
<223> OTHER INFORMATION: n = A, T, C, or G
<220> FEATURE:
<221> NAME/KEY: unsure
<222> LOCATION: (393)
<223> OTHER INFORMATION: n = A, T, C, or G
<220> FEATURE:
<221> NAME/KEY: unsure
<222> LOCATION: (396)..(397)
<223> OTHER INFORMATION: n = A, T, C, or G
<220> FEATURE:
<221> NAME/KEY: unsure
<222> LOCATION: (408)
<223> OTHER INFORMATION: n = A, T, C, or G
<220> FEATURE:
<221> NAME/KEY: unsure
<222> LOCATION: (413)
<223> OTHER INFORMATION: n = A, T, C, or G
<220> FEATURE:
<221> NAME/KEY: unsure
<222> LOCATION: (418)
<223> OTHER INFORMATION: n = A, T, C, or G
<220> FEATURE:
<221> NAME/KEY: unsure
<222> LOCATION: (423)
<223> OTHER INFORMATION: n = A, T, C, or G

<400> SEQUENCE: 9

```
gctgtgaggt cgccgaaggc gtgcgcgatc aagttcccca ccctcgtctc gcaagggctg      60
ctcttcgtgt ggcccgacga gaatgggtgg gagaaggcca cggctaccaa gcctccgatg     120
ttaccgaagg agtttgagga tcctgcgttc tccacggtga ccatccagag ggatctgtac     180
tatggctatg atacattgat ggagaacgtc tctgatccgt cgcatataga atttgctcac     240
cacaaggtca ctgggtcgaa gagatcgaan caagcctttt gccaattcaa gaatgggaat     300
caaagttggt gcaatggggg ataattcaag gggtcaaatt tctgggaaaa ccctccgcat     360
caagtggcaa cttttttgtn ggccccttg  ccnatnncac ttgaaacnaa aanttggnga     420
atnaga                                                                426
```

<210> SEQ ID NO 10
<211> LENGTH: 107
<212> TYPE: PRT
<213> ORGANISM: Oryza sativa
<220> FEATURE:
<221> NAME/KEY: UNSURE
<222> LOCATION: (90)
<223> OTHER INFORMATION: Xaa = any amino acid -continued

```
<400> SEQUENCE: 10

Ala Val Arg Ser Pro Lys Ala Cys Ala Ile Lys Phe Pro Thr Leu Val
  1               5                  10                  15

Ser Gln Gly Leu Leu Phe Val Trp Pro Asp Glu Asn Gly Trp Glu Lys
                 20                  25                  30

Ala Thr Ala Thr Lys Pro Pro Met Leu Pro Lys Glu Phe Glu Asp Pro
             35                  40                  45

Ala Phe Ser Thr Val Thr Ile Gln Arg Asp Leu Tyr Tyr Gly Tyr Asp
         50                  55                  60

Thr Leu Met Glu Asn Val Ser Asp Pro Ser His Ile Glu Phe Ala His
 65                  70                  75                  80

His Lys Val Thr Gly Ser Lys Arg Ser Xaa Gln Ala Phe Cys Gln Phe
                 85                  90                  95

Lys Asn Gly Asn Gln Ser Trp Cys Asn Gly Gly
            100                 105

<210> SEQ ID NO 11
<211> LENGTH: 465
<212> TYPE: DNA
<213> ORGANISM: Glycine max
<220> FEATURE:
<221> NAME/KEY: unsure
<222> LOCATION: (460)
<223> OTHER INFORMATION: n = A, T, C, or G

<400> SEQUENCE: 11
aaaccattga tggcgctccc tcactccatc tctgccttag ccaccacact cacactctcc    60
tccccaataa ccaaaccccca taaagttaac cctttccct tttcctcgaa ccgaaattca   120 caattttttaa cgaaacaaac gcgacccaga agcagaagaa acctctccct aaccctgca   180 cgcgttgcgg cgccaccctc aacggttgaa gccgatcgat tatacccaga ggccgaaaat   240
aacgaaactg aggaagagtt tagcgacgag agctcttcct ctaaattcac ttggagggat   300
cactggtacc ctgtctcgtt aattgaagat ctgaaccctc tcttgcccac accgtttcag   360
cttctgggtc gtgaaatcgt gctctggtac gacaagtcca tttcccaatg ggttgctttt   420
gatgacaaat gccccatcg tcttgcccct ttatctgaan ggagg              465

<210> SEQ ID NO 12
<211> LENGTH: 66
<212> TYPE: PRT
<213> ORGANISM: Glycine max
<220> FEATURE:
<221> NAME/KEY: UNSURE
<222> LOCATION: (65)
<223> OTHER INFORMATION: Xaa = any amino acid

<400> SEQUENCE: 12

Glu Ser Ser Ser Lys Phe Thr Trp Arg Asp His Trp Tyr Pro Val
  1               5                  10                  15

Ser Leu Ile Glu Asp Leu Asn Pro Leu Leu Pro Thr Pro Phe Gln Leu
                 20                  25                  30

Leu Gly Arg Glu Ile Val Leu Trp Tyr Asp Lys Ser Ile Ser Gln Trp
             35                  40                  45

Val Ala Phe Asp Asp Lys Cys Pro His Arg Leu Ala Pro Leu Ser Glu
         50                  55                  60

Xaa Arg
 65
```

```
<210> SEQ ID NO 13
<211> LENGTH: 558
<212> TYPE: DNA
<213> ORGANISM: Triticum aestivum
<220> FEATURE:
<221> NAME/KEY: unsure
<222> LOCATION: (207)
<223> OTHER INFORMATION: n = A, T, C, or G
<220> FEATURE:
<221> NAME/KEY: unsure
<222> LOCATION: (216)
<223> OTHER INFORMATION: n = A, T, C, or G
<220> FEATURE:
<221> NAME/KEY: unsure
<222> LOCATION: (249)
<223> OTHER INFORMATION: n = A, T, C, or G
<220> FEATURE:
<221> NAME/KEY: unsure
<222> LOCATION: (254)
<223> OTHER INFORMATION: n = A, T, C, or G
<220> FEATURE:
<221> NAME/KEY: unsure
<222> LOCATION: (269)
<223> OTHER INFORMATION: n = A, T, C, or G
<220> FEATURE:
<221> NAME/KEY: unsure
<222> LOCATION: (294)
<223> OTHER INFORMATION: n = A, T, C, or G
<220> FEATURE:
<221> NAME/KEY: unsure
<222> LOCATION: (310)
<223> OTHER INFORMATION: n = A, T, C, or G
<220> FEATURE:
<221> NAME/KEY: unsure
<222> LOCATION: (330)
<223> OTHER INFORMATION: n = A, T, C, or G
<220> FEATURE:
<221> NAME/KEY: unsure
<222> LOCATION: (335)
<223> OTHER INFORMATION: n = A, T, C, or G
<220> FEATURE:
<221> NAME/KEY: unsure
<222> LOCATION: (339)..(340)
<223> OTHER INFORMATION: n = A, T, C, or G
<220> FEATURE:
<221> NAME/KEY: unsure
<222> LOCATION: (365)
<223> OTHER INFORMATION: n = A, T, C, or G
<220> FEATURE:
<221> NAME/KEY: unsure
<222> LOCATION: (386)
<223> OTHER INFORMATION: n = A, T, C, or G
<220> FEATURE:
<221> NAME/KEY: unsure
<222> LOCATION: (404)
<223> OTHER INFORMATION: n = A, T, C, or G
<220> FEATURE:
<221> NAME/KEY: unsure
<222> LOCATION: (406)
<223> OTHER INFORMATION: n = A, T, C, or G
<220> FEATURE:
<221> NAME/KEY: unsure
<222> LOCATION: (445)
<223> OTHER INFORMATION: n = A, T, C, or G
<220> FEATURE:
<221> NAME/KEY: unsure
<222> LOCATION: (451)
<223> OTHER INFORMATION: n = A, T, C, or G
<220> FEATURE:
<221> NAME/KEY: unsure
<222> LOCATION: (462)
<223> OTHER INFORMATION: n = A, T, C, or G
<220> FEATURE:
<221> NAME/KEY: unsure
<222> LOCATION: (470)
<223> OTHER INFORMATION: n = A, T, C, or G
<220> FEATURE:
<221> NAME/KEY: unsure
<222> LOCATION: (475)
```

<223> OTHER INFORMATION: n = A, T, C, or G
<220> FEATURE:
<221> NAME/KEY: unsure
<222> LOCATION: (483)..(484)
<223> OTHER INFORMATION: n = A, T, C, or G
<220> FEATURE:
<221> NAME/KEY: unsure
<222> LOCATION: (490)
<223> OTHER INFORMATION: n = A, T, C, or G
<220> FEATURE:
<221> NAME/KEY: unsure
<222> LOCATION: (496)
<223> OTHER INFORMATION: n = A, T, C, or G
<220> FEATURE:
<221> NAME/KEY: unsure
<222> LOCATION: (498)
<223> OTHER INFORMATION: n = A, T, C, or G
<220> FEATURE:
<221> NAME/KEY: unsure
<222> LOCATION: (511)
<223> OTHER INFORMATION: n = A, T, C, or G
<220> FEATURE:
<221> NAME/KEY: unsure
<222> LOCATION: (514)
<223> OTHER INFORMATION: n = A, T, C, or G
<220> FEATURE:
<221> NAME/KEY: unsure
<222> LOCATION: (520)
<223> OTHER INFORMATION: n = A, T, C, or G
<220> FEATURE:
<221> NAME/KEY: unsure
<222> LOCATION: (522)
<223> OTHER INFORMATION: n = A, T, C, or G
<220> FEATURE:
<221> NAME/KEY: unsure
<222> LOCATION: (528)
<223> OTHER INFORMATION: n = A, T, C, or G
<220> FEATURE:
<221> NAME/KEY: unsure
<222> LOCATION: (533)
<223> OTHER INFORMATION: n = A, T, C, or G
<220> FEATURE:
<221> NAME/KEY: unsure
<222> LOCATION: (545)
<223> OTHER INFORMATION: n = A, T, C, or G

<400> SEQUENCE: 13

```
ccagggcctg ctcttcgtct ggcctgacga gaatggatgg gacaaggcca aggccaccaa      60
gcctccaatg ctgccgaagg agttcgatga cccggccttc tccaccgtga cgatccagag     120
ggacctcttc tatgggtatg acacgttgat ggagaacgtc tctgatccct cgcatataga     180
atttgctcac cacaaggtca ctggacnaag agatanagcc aagcctttgc catttaaaat     240
ggaatcaant ggcncatggg gatattcang ggcaaatacc ggcaatcctc gcancactgc     300
aactttcgan gccccttggc tatgcactgn aacanaattn agattgacac caaattaacc     360
gattntggga gatcacaaat gggtcntatg gatttgctcc ttcnanattc caaaggccca     420
aggaaaatcg ttctattgtc cgtantgctc naaactttc antttaaatn ccacnaagga     480
tgnngaattn tccccnantg tacaacattg ngcncaattn gncatgangc aantatctct     540
tcagncacaa agttccgt                                                   558
```

<210> SEQ ID NO 14
<211> LENGTH: 105
<212> TYPE: PRT
<213> ORGANISM: Triticum aestivum
<220> FEATURE:
<221> NAME/KEY: UNSURE
<222> LOCATION: (69)
<223> OTHER INFORMATION: Xaa = any amino acid
<220> FEATURE:
<221> NAME/KEY: UNSURE
<222> LOCATION: (72)
<223> OTHER INFORMATION: Xaa = any amino acid
<220> FEATURE:
<221> NAME/KEY: UNSURE
<222> LOCATION: (83)
<223> OTHER INFORMATION: Xaa = any amino acid
<220> FEATURE:
<221> NAME/KEY: UNSURE
<222> LOCATION: (85)
<223> OTHER INFORMATION: Xaa = any amino acid
<220> FEATURE:
<221> NAME/KEY: UNSURE
<222> LOCATION: (90)
<223> OTHER INFORMATION: Xaa = any amino acid
<220> FEATURE:
<221> NAME/KEY: UNSURE
<222> LOCATION: (98)
<223> OTHER INFORMATION: Xaa = any amino acid
<220> FEATURE:
<221> NAME/KEY: UNSURE
<222> LOCATION: (103)
<223> OTHER INFORMATION: Xaa = any amino acid

<400> SEQUENCE: 14

```
Gln Gly Leu Leu Phe Val Trp Pro Asp Glu Asn Gly Trp Asp Lys Ala
 1               5                  10                  15

Lys Ala Thr Lys Pro Pro Met Leu Pro Lys Glu Phe Asp Asp Pro Ala
            20                  25                  30

Phe Ser Thr Val Thr Ile Gln Arg Asp Leu Phe Tyr Gly Tyr Asp Thr
        35                  40                  45

Leu Met Glu Asn Val Ser Asp Pro Ser His Ile Glu Phe Ala His His
    50                  55                  60

Lys Val Thr Gly Xaa Arg Asp Xaa Ala Lys Pro Leu Pro Phe Lys Met
65                  70                  75                  80

Glu Ser Xaa Gly Xaa Trp Gly Tyr Ser Xaa Ala Asn Thr Gly Asn Pro
            85                  90                  95

Arg Xaa Thr Ala Thr Phe Xaa Ala Pro
        100                 105
```

<210> SEQ ID NO 15
<211> LENGTH: 562
<212> TYPE: DNA
<213> ORGANISM: Zea mays
<220> FEATURE:
<221> NAME/KEY: unsure
<222> LOCATION: (136)
<223> OTHER INFORMATION: n = A, T, C, or G
<220> FEATURE:
<221> NAME/KEY: unsure
<222> LOCATION: (562)
<223> OTHER INFORMATION: n = A, T, C, or G

<400> SEQUENCE: 15

```
cgccgtgctc gtccgcgcgc gcgccacatg ctacaggtgc tcaagctcga caagtgctcc    60
ggcttctcaa cggacgccct ccgcctcgtc gcccgctcct gcagatctct gagaactttg   120
ttcctggaag aatgtntaat tgccgatgaa gggagcgaat ggctccatga actcgccgtc   180
aacaattctg ttctggtgac actgaacttc tacatgacag aactcaaagt ggagcctgcc   240
gatctggagc ttcttgcaag gaactgtaaa tcattgattt ctctgaagat gagtgactgc   300
gatctttcgg atttgatggt tttctccaaa cctccaaggc actgcaagaa ttcgctggag   360
gcgcttttt cgaaatcgga gagtacacca agtacgaaaa ggtcaagctc ccacctaagc   420
tatgcttctt gggggtcttt accttcatgg gtaaaaacga gatgcccgtt aatctttccg   480
tattctgcgt tcgcttaaga aactggacct gcagtacact ttccctcacc actgaagatc   540
```

```
actgtcagct taatcgctaa an                                              562
```

<210> SEQ ID NO 16
<211> LENGTH: 186
<212> TYPE: PRT
<213> ORGANISM: Zea mays
<220> FEATURE:
<221> NAME/KEY: UNSURE
<222> LOCATION: (46)
<223> OTHER INFORMATION: Xaa = any amino acid
<220> FEATURE:
<221> NAME/KEY: UNSURE
<222> LOCATION: (111)
<223> OTHER INFORMATION: Xaa = any amino acid

<400> SEQUENCE: 16

```
Arg Arg Ala Arg Pro Arg Ala Arg His Met Leu Gln Val Leu Lys Leu
 1               5                  10                  15

Asp Lys Cys Ser Gly Phe Ser Thr Asp Ala Leu Arg Leu Val Ala Arg
            20                  25                  30

Ser Cys Arg Ser Leu Arg Thr Leu Phe Leu Glu Glu Cys Xaa Ile Ala
        35                  40                  45

Asp Glu Gly Ser Glu Trp Leu His Glu Leu Ala Val Asn Asn Ser Val
    50                  55                  60

Leu Val Thr Leu Asn Phe Tyr Met Thr Glu Leu Lys Val Glu Pro Ala
65                  70                  75                  80

Asp Leu Glu Leu Leu Ala Arg Asn Cys Lys Ser Leu Ile Ser Leu Lys
                85                  90                  95

Met Ser Asp Cys Asp Leu Ser Asp Leu Met Val Phe Ser Lys Xaa Ser
            100                 105                 110

Lys Ala Leu Gln Glu Phe Ala Gly Gly Ala Phe Phe Glu Ile Gly Glu
        115                 120                 125

Tyr Thr Lys Tyr Glu Lys Val Lys Leu Pro Pro Lys Leu Cys Phe Leu
    130                 135                 140

Gly Gly Leu Thr Phe Met Gly Lys Asn Glu Met Pro Val Asn Leu Ser
145                 150                 155                 160

Val Phe Cys Val Arg Leu Arg Asn Trp Thr Cys Ser Thr Leu Ser Leu
                165                 170                 175

Thr Thr Glu Asp His Cys Gln Leu Asn Arg
            180                 185
```

<210> SEQ ID NO 17
<211> LENGTH: 1728
<212> TYPE: DNA
<213> ORGANISM: Zea mays

<400> SEQUENCE: 17

```
ccacgcgtcc gcggacgcgt gggctggaaa cacttttcct ggaagaaagc acaattgatg    60
agaaagaaaa tgatgagtgg atccgtgagc ttgctacgag caattctgtt cttgagacac   120
tgaatttctt tctaacagat ctcagggcat ccccagagta tcttaccctc cttgtgcgca   180
actgtcaacg attgaaaact ctgaagatta gtgaatgttt catgcccgat ctggtcagtt   240
tgttccgaac tgcacaaaca ctacaagagt tcgctggtgg ttcctttgaa gagcagggtc   300
aacctgtggc aagtagaaat tatgagaact actattttcc tccttcactg caccgcttga   360
gtttgctcta catgggaaca aatgatatgc aaatactgtt tccatatgct actgcactta   420
agaagttaga ccttcagttt acattccttt ccacagagga tcattgtcag atagttcaac   480
```

```
gctgctccaa tctggaaacc ttagaggtga gggatgtcat aggggatcgt ggactacaag    540
ttgttgcaca gacctgcaag aaattgcata ggctcagagt agagagagga gatgatgatc    600
aaggaggtct tgaggatgaa caaggtagga tttcacaggt ggggttgatg gctatagccc    660
aaggctgccc tgagttgaca tactgggcga tacatgtatc agacattaca aatgcagctt    720
tagaggcagt tggtacatgc agcaaaaatc ttaatgactt ccgccttgtc ctccttgata    780
gagaagcaca tataaccgaa ttgccactgg acaatgggt tcgtgctttg cttagaggtt     840
gcaccaaact acggaggttt gcattttatg tgagacctgg ggcctatct gatgttggtc     900 ttggctatgt tggagaattt agtaagagta ttcgttatat gttgcttggt aatgttggtg    960
aatctgataa tggaatcata caattatcaa aaggctgccc aagcttgcaa aaactggagg   1020
tgaggggttg tctctttagt gagcatgctt tagctttggc tgcactacag cttaagtcac   1080
tgaggtatct gtgggtacaa ggattcaggt catctccaac tggaactgat attatggcaa   1140
tggtacgccc cttctggaac attgagtata ttgttccaga tcaagatgaa ccttgcccag   1200
agcataagag acagattctg gcatactact cccttgctgg caggaggaca gattgtcctc   1260
catcagtaac tctgctttac ccggcatttt gagtgtagat acttgctttt tgccagactg   1320
aatctcatgg tactaagttc cattggtccc actatctgtg aagtaaatgg tccctgttct   1380
tccaattgat gaggacatgc agacgttcca gtgcaaagaa ccccaaaggt aagctttaag   1440
caggacggcc agctctgaac tgaggctagc tgagaacaat catgaatacc tgaaggcagc   1500
acttatgtca gcttggccta gctgtccagt atgggcatgt aagctttacc atcttttgta   1560
gttttggaga acaattttg caataactac ccttgtttag tgtatattat cgattttcgt    1620
tcatatgctg ttgtattgtt gtattgaaca attatgtcaa ttaattagtc tacactctac   1680
agtctaaaaa aaaaaaaaaa aaaaaaaaaa aaaaaaaaa aaaaaaag                 1728
```

<210> SEQ ID NO 18
<211> LENGTH: 429
<212> TYPE: PRT
<213> ORGANISM: Zea mays

<400> SEQUENCE: 18

```
Thr Arg Pro Arg Thr Arg Gly Leu Glu Thr Leu Phe Leu Glu Glu Ser
  1               5                  10                  15

Thr Ile Asp Glu Lys Glu Asn Asp Glu Trp Ile Arg Glu Leu Ala Thr
                 20                  25                  30

Ser Asn Ser Val Leu Glu Thr Leu Asn Phe Phe Leu Thr Asp Leu Arg
         35                  40                  45

Ala Ser Pro Glu Tyr Leu Thr Leu Leu Val Arg Asn Cys Gln Arg Leu
     50                  55                  60

Lys Thr Leu Lys Ile Ser Glu Cys Phe Met Pro Asp Leu Val Ser Leu
 65                  70                  75                  80

Phe Arg Thr Ala Gln Thr Leu Gln Glu Phe Ala Gly Gly Ser Phe Glu
                 85                  90                  95

Glu Gln Gly Gln Pro Val Ala Ser Arg Asn Tyr Glu Asn Tyr Tyr Phe
            100                 105                 110

Pro Pro Ser Leu His Arg Leu Ser Leu Leu Tyr Met Gly Thr Asn Asp
        115                 120                 125

Met Gln Ile Leu Phe Pro Tyr Ala Thr Ala Leu Lys Lys Leu Asp Leu
    130                 135                 140

Gln Phe Thr Phe Leu Ser Thr Glu Asp His Cys Gln Ile Val Gln Arg
145                 150                 155                 160
```

Cys Ser Asn Leu Glu Thr Leu Glu Val Arg Asp Val Ile Gly Asp Arg
            165                 170                 175

Gly Leu Gln Val Val Ala Gln Thr Cys Lys Lys Leu His Arg Leu Arg
        180                 185                 190

Val Glu Arg Gly Asp Asp Asp Gln Gly Gly Leu Glu Asp Glu Gln Gly
            195                 200                 205

Arg Ile Ser Gln Val Gly Leu Met Ala Ile Ala Gln Gly Cys Pro Glu
    210                 215                 220

Leu Thr Tyr Trp Ala Ile His Val Ser Asp Ile Thr Asn Ala Ala Leu
225                 230                 235                 240

Glu Ala Val Gly Thr Cys Ser Lys Asn Leu Asn Asp Phe Arg Leu Val
                245                 250                 255

Leu Leu Asp Arg Glu Ala His Ile Thr Glu Leu Pro Leu Asp Asn Gly
            260                 265                 270

Val Arg Ala Leu Leu Arg Gly Cys Thr Lys Leu Arg Arg Phe Ala Phe
    275                 280                 285

Tyr Val Arg Pro Gly Ala Leu Ser Asp Val Gly Leu Gly Tyr Val Gly
290                 295                 300

Glu Phe Ser Lys Ser Ile Arg Tyr Met Leu Leu Gly Asn Val Gly Glu
305                 310                 315                 320

Ser Asp Asn Gly Ile Ile Gln Leu Ser Lys Gly Cys Pro Ser Leu Gln
                325                 330                 335

Lys Leu Glu Val Arg Gly Cys Leu Phe Ser Glu His Ala Leu Ala Leu
            340                 345                 350

Ala Ala Leu Gln Leu Lys Ser Leu Arg Tyr Leu Trp Val Gln Gly Phe
    355                 360                 365

Arg Ser Ser Pro Thr Gly Thr Asp Ile Met Ala Met Val Arg Pro Phe
370                 375                 380

Trp Asn Ile Glu Tyr Ile Val Pro Asp Gln Asp Glu Pro Cys Pro Glu
385                 390                 395                 400

His Lys Arg Gln Ile Leu Ala Tyr Tyr Ser Leu Ala Gly Arg Arg Thr
                405                 410                 415

Asp Cys Pro Pro Ser Val Thr Leu Leu Tyr Pro Ala Phe
            420                 425

<210> SEQ ID NO 19
<211> LENGTH: 2240
<212> TYPE: DNA
<213> ORGANISM: Oryza sativa

<400> SEQUENCE: 19
cccccgggct gcaggaattc ggcacgagct ctcccttctc ctcctcttca ccaccaccac      60
caccaccagc agcagcagag agcaccatct ccatccaata atccccatgc ttgcgcacca     120
ctcccggcca catcccgcgc gaggaggagg aggaggagga gggtgtgctt gatccgcgct     180
cccgcctggt tggtggtggt ggggtgaggg gggagggatg ggaggggagg caccggaggc     240
gcggcggttg gaccgcgcga tgagcttcgg cggcgcgggc agcatcccgg aggaggcgct     300
gcacctggtg ctgggtacg tggacgaccc gcgggacagg gaggcggtgt cgctcgtgtg     360
ccgccgctgg caccgcatcg acgcgctcac gcggaagcac gtcaccgtgc ccttctgcta     420
cgccgcgtcg cccgcgcacc tgctcgcgcg gttcccgcgg ctggagtcgc tcgcggtcaa     480
ggggaagccg cgcgccgcca tgtacgggct catcccggag gactgggcg cctacgcgcg     540 cccctgggtc gccgagctcg ccgcgccgct cgagtgcctc aaggcgctcc acctgcgccg     600

-continued

```
catggtcgtc accgacgacg acctcgccgc gctcgtccgc gcccgcggcc acatgctgca    660
ggagctcaag ctcgacaagt gctccggctt ctccaccgac gctctccgcc tcgtcgcccg    720
ctcctgcaga tcactgagaa cattatttct ggaggaatgc tcaattgctg ataatggtac    780
tgaatggctc cacgaccttg ctgtcaacaa tcctgttctg agacattga acttccacat     840
gaccgaactc acagtggtgc cagctgacct ggagcttctc gcaaagaagt gcaagtcact    900
aatttcattg aagatcagtg actgtgactt ttcagattta attggatttt ccggatggc     960
tgcatcattg caagagtttg cggggagggc attcattgag caaggggagc tcactaagta    1020
tggaaatgtt aaattcccct caagactgtg ctccttagga cttacgtaca tggggacaaa    1080
cgagatgccc attatcttcc ctttctctgc attactcaag aagctggact tgcagtacac    1140
ttttctcacc actgaagatc actgccaact cattgcaaaa tgtcccaact tactagttct    1200
tgcggtgagg aatgtgattg gagatagagg attaggggtt gttgcagaca catgcaagaa    1260
gctacaaaga ctcagagttg agcgaggaga tgatgatcca ggtttgcaag aagaacaagg    1320
aggagtctct caagtcgggt tgacaactgt agccgtagga tgccgtgaac tggaatacat    1380
agctgcctat gtgtctgata tcacaaatgg ggccctggag tctattggga ctttctgcaa    1440
aaatctttgc gacttccgtc ttgtcctact cgatagagaa gagaggataa cagatttgcc    1500
cttagacaat ggtgtccgtg cactgctgag ggctgcacg aaacttcgga ggtttgctct     1560
atacttgaga ccaggggggac tttcagatac aggccttggc tatattggac agtacagtgg    1620
aattatccaa tacatgcttc tgggtaatgt tggggaaaca gatgatggtc tgatccggtt    1680
tgcattgggg tgtgagaacc tgcggaagct tgagctaagg agttgttgct tcagtgagca    1740
agctttagcc cgcgctatac ggagtatgcc ttccctgaga tacgtgtggg tacagggcta    1800
caaggcttct aagactggtc acgatctcat gctcatggcc aggcccttct ggaacataga    1860
gtttacacct cccagttctg agaatgcaaa tcgaatgaga gaagatggtg aaccttgtgt    1920
agatagtcaa gctcagatac ttgcatacta ctcccttgcc gggaagaggt cggactgccc    1980
acgatctgtg gttcctttgt atcctgcgtg actgtaaata ccgatatggt atctctctgc    2040
ttcgttcttg cctcttgcct ttttggggtg atatgttgat atgtggttat tgtatgggtc    2100
tagaactcta gatggctagc tgctatgtac sgtaataagc tactggtagc tgagatgtac    2160
tggaataagc acttctattt cccactctaa aaaaaaaaa aaaactcgg gcacgagggg     2220
gggcccggta cccaattcgc                                                2240
```

<210> SEQ ID NO 20
<211> LENGTH: 597
<212> TYPE: PRT
<213> ORGANISM: Oryza sativa

<400> SEQUENCE: 20

```
Met Gly Gly Glu Ala Pro Glu Ala Arg Arg Leu Asp Arg Ala Met Ser
 1               5                  10                  15

Phe Gly Ala Gly Ser Ile Pro Glu Glu Ala Leu His Leu Val Leu
            20                  25                  30

Gly Tyr Val Asp Asp Pro Arg Asp Arg Glu Ala Val Ser Leu Val Cys
        35                  40                  45

Arg Arg Trp His Arg Ile Asp Ala Leu Thr Arg Lys His Val Thr Val
    50                  55                  60

Pro Phe Cys Tyr Ala Ala Ser Pro Ala His Leu Leu Ala Arg Phe Pro
65                  70                  75                  80
```

-continued

```
Arg Leu Glu Ser Leu Ala Val Lys Gly Lys Pro Arg Ala Ala Met Tyr
                 85                  90                  95
Gly Leu Ile Pro Glu Asp Trp Gly Ala Tyr Ala Arg Pro Trp Val Ala
            100                 105                 110
Glu Leu Ala Ala Pro Leu Glu Cys Leu Lys Ala Leu His Leu Arg Arg
        115                 120                 125
Met Val Val Thr Asp Asp Leu Ala Ala Leu Val Arg Ala Arg Gly
    130                 135                 140
His Met Leu Gln Glu Leu Lys Leu Asp Lys Cys Ser Gly Phe Ser Thr
145                 150                 155                 160
Asp Ala Leu Arg Leu Val Ala Arg Ser Cys Arg Ser Leu Arg Thr Leu
                165                 170                 175
Phe Leu Glu Glu Cys Ser Ile Ala Asp Asn Gly Thr Glu Trp Leu His
            180                 185                 190
Asp Leu Ala Val Asn Asn Pro Val Leu Glu Thr Leu Asn Phe His Met
        195                 200                 205
Thr Glu Leu Thr Val Val Pro Ala Asp Leu Glu Leu Leu Ala Lys Lys
    210                 215                 220
Cys Lys Ser Leu Ile Ser Leu Lys Ile Ser Asp Cys Asp Phe Ser Asp
225                 230                 235                 240
Leu Ile Gly Phe Phe Arg Met Ala Ala Ser Leu Gln Glu Phe Ala Gly
                245                 250                 255
Gly Ala Phe Ile Glu Gln Gly Glu Leu Thr Lys Tyr Gly Asn Val Lys
            260                 265                 270
Phe Pro Ser Arg Leu Cys Ser Leu Gly Leu Thr Tyr Met Gly Thr Asn
        275                 280                 285
Glu Met Pro Ile Ile Phe Pro Phe Ser Ala Leu Leu Lys Lys Leu Asp
    290                 295                 300
Leu Gln Tyr Thr Phe Leu Thr Thr Glu Asp His Cys Gln Leu Ile Ala
305                 310                 315                 320
Lys Cys Pro Asn Leu Leu Val Leu Ala Val Arg Asn Val Ile Gly Asp
                325                 330                 335
Arg Gly Leu Gly Val Val Ala Asp Thr Cys Lys Lys Leu Gln Arg Leu
            340                 345                 350
Arg Val Glu Arg Gly Asp Asp Pro Gly Leu Gln Glu Glu Gln Gly
        355                 360                 365
Gly Val Ser Gln Val Gly Leu Thr Thr Val Ala Val Gly Cys Arg Glu
    370                 375                 380
Leu Glu Tyr Ile Ala Ala Tyr Val Ser Asp Ile Thr Asn Gly Ala Leu
385                 390                 395                 400
Glu Ser Ile Gly Thr Phe Cys Lys Asn Leu Cys Asp Phe Arg Leu Val
                405                 410                 415
Leu Leu Asp Arg Glu Glu Arg Ile Thr Asp Leu Pro Leu Asp Asn Gly
            420                 425                 430
Val Arg Ala Leu Leu Arg Gly Cys Thr Lys Leu Arg Arg Phe Ala Leu
        435                 440                 445
Tyr Leu Arg Pro Gly Gly Leu Ser Asp Thr Gly Leu Gly Tyr Ile Gly
    450                 455                 460
Gln Tyr Ser Gly Ile Ile Gln Tyr Met Leu Leu Gly Asn Val Gly Glu
465                 470                 475                 480
Thr Asp Asp Gly Leu Ile Arg Phe Ala Leu Gly Cys Glu Asn Leu Arg
                485                 490                 495
```

-continued

```
              Lys Leu Glu Leu Arg Ser Cys Cys Phe Ser Glu Gln Ala Leu Ala Arg
                          500                 505                 510

Ala Ile Arg Ser Met Pro Ser Leu Arg Tyr Val Trp Val Gln Gly Tyr
                      515                 520                 525

Lys Ala Ser Lys Thr Gly His Asp Leu Met Leu Met Ala Arg Pro Phe
                      530                 535                 540

Trp Asn Ile Glu Phe Thr Pro Pro Ser Glu Asn Ala Asn Arg Met
              545                 550                 555                 560

Arg Glu Asp Gly Glu Pro Cys Val Asp Ser Gln Ala Gln Ile Leu Ala
                              565                 570                 575

Tyr Tyr Ser Leu Ala Gly Lys Arg Ser Asp Cys Pro Arg Ser Val Val
                          580                 585                 590

Pro Leu Tyr Pro Ala
                          595

<210> SEQ ID NO 21
<211> LENGTH: 2288
<212> TYPE: DNA
<213> ORGANISM: Glycine max

<400> SEQUENCE: 21
gcacgaggcc acacgttaca caggcgacta tggttgccgg aaacaaatcc ggatgggaaa      60
gggtgtatgt agctgttcct aggatgaata ttgtgataac agaacggcgt ttgaagcagt     120
gacgtgttac atcagtacat cacatcacat cacgtaaata taggtaataa gctcggaaaa     180
agttttgtcg tttcacaccc atctgtttgg ccctaccatt tcctcactca tcatccccat     240
aacccattcc ccttttgcca cttgaaccaa aacctctgca ccttttcttt tcactctcag     300
tctccgatcc aatatgacgg aggaacggaa cgtgcggaag acacgtgtgg tcgacgtggt     360
cctcgactgc gtcatccctt acatcgacga ccccaaggac cgcgacgccg tttcccaggt     420
gtgtcgacgc tggtacgagc tcgactcgct cacccgcaag cacgtcacca tcgcgctctg     480
ctacaccacc accccggctc gcctccgccg ccgcttcccg cacctcgagt cgctcaagct     540
caagggcaag ccccgagccg caatgttcaa cttgataccc gaggattggg gcggacacgt     600
cactccctgg gtcaaagaga tttctcagta cttcgattgc ctcaagagcc tccacttccg     660
ccgcatgatt gtcaaggatt ccgatcttca gaatctcgct cgtgaccgcg gtcacgtgct     720
tcacgctctc aagcttgaca agtgctccgg tttcaccacc gatggtcttt tccatatcgg     780
tcgcttttgc aagagtttaa gagtcttgtt tttggaggaa agctcaattc ttgagaagga     840
cggagaatgg ctacacgagc ttgctttgaa taatacagtt cttgagactc tcaattttta     900
cttgacagac attgctgttg tgaagattga ggaccttgaa cttttagcta aaaattgccc     960
caacttagtg tctgtgaaac ttactgactg tgaaatactg gatcttgtga acttctttaa    1020
gcatgcctct gcgctggaag agttttgtgg aggcacctac aacgaggaac agaaagata    1080 ctctgctata tcattaccag caaagttatg tcgattgggt ttaacatata ttggaaagaa    1140
tgagttgccc attgtgttca tgtttgcagc cgtactaaaa aaattggatc tcctctatgc    1200
aatgctagac acggaggatc attgtatgtt aatccaaagg tgtccaaatc tggaagtcct    1260
tgagacaagg aatgtaattg gagatagagg gttagaggtt cttggtcgtt gttgtaagag    1320
gctaaaaagg cttaggattg aaaggggcga tgatgatcaa ggaatggagg atgaagaagg    1380
tactgtgtcc catagagggc taatagcctt gtcacagggc tgttcagagc ttgaatacat    1440
ggctgtttat gtgtctgata ttacaaatgc atctctggaa catattggaa ctcacttgaa    1500
```

-continued

```
gaacctctgt gatttcgcc ttgtgttgct tgaccatgaa gagaagataa ctgatttgcc    1560
acttgacaat ggggtgaggg ctctactgag gggctgtgac aagctgagga gatttgctct    1620
atatctcagg cgtggcgggt tgactgatgt aggccttggt tacattggac aatacagtcc    1680
aaatgtgaga tggatgctgc ttggttatgt gggggagtct gatgcagggc ttttggagtt    1740
cgctaagggg tgtcctagtc ttcagaaact tgaaatgaga gggtgtttat ttttcagtga    1800
acgtgcactt gctgtggctg caacacaatt gacttctctt aggtacttgt gggtgcaagg    1860
ttatggtgta tctccatctg gacgtgatct tttggtaatg gctcgaccct tttggaacat    1920
tgagttgatt ccttctagaa aggtggctac gaataccaat ccagatgaga ctgtagttgt    1980
tgagcatcct gctcatattc ttgcatatta ttctcttgca gggcagagat cagattttcc    2040
agatactgtt gtgcctttgg acactgccac atgcgttgat acctagaggc cagagctgtg    2100
tatatatacc agttttcttt tgttttctt ctccccttc atatgctgtt tctatgttcc     2160
tgctctattt gtagttcatt ttagacaatt agtcttgtaa taagcctgtg ttttcatttg    2220
aaattctgaa acgcttcccc taacgctatt ggctcccta aaaactgaac attctcaatt     2280
ttgtgaat                                                             2288
```

<210> SEQ ID NO 22
<211> LENGTH: 606
<212> TYPE: PRT
<213> ORGANISM: Glycine max

<400> SEQUENCE: 22

```
Thr Lys Thr Ser Ala Pro Phe Leu Phe Thr Leu Ser Leu Arg Ser Asn
  1               5                  10                  15

Met Thr Glu Glu Arg Asn Val Arg Lys Thr Arg Val Val Asp Val Val
             20                  25                  30

Leu Asp Cys Val Ile Pro Tyr Ile Asp Asp Pro Lys Asp Arg Asp Ala
         35                  40                  45

Val Ser Gln Val Cys Arg Arg Trp Tyr Glu Leu Asp Ser Leu Thr Arg
     50                  55                  60

Lys His Val Thr Ile Ala Leu Cys Tyr Thr Thr Pro Ala Arg Leu
 65                  70                  75                  80

Arg Arg Arg Phe Pro His Leu Glu Ser Leu Lys Leu Gly Lys Pro
                 85                  90                  95

Arg Ala Ala Met Phe Asn Leu Ile Pro Glu Asp Trp Gly His Val
            100                 105                 110

Thr Pro Trp Val Lys Glu Ile Ser Gln Tyr Phe Asp Cys Leu Lys Ser
        115                 120                 125

Leu His Phe Arg Arg Met Ile Val Lys Asp Ser Asp Leu Gln Asn Leu
    130                 135                 140

Ala Arg Asp Arg Gly His Val Leu His Ala Leu Lys Leu Asp Lys Cys
145                 150                 155                 160

Ser Gly Phe Thr Thr Asp Gly Leu Phe His Ile Gly Arg Phe Cys Lys
                165                 170                 175

Ser Leu Arg Val Leu Phe Leu Glu Glu Ser Ser Ile Leu Glu Lys Asp
            180                 185                 190

Gly Glu Trp Leu His Glu Leu Ala Leu Asn Asn Thr Val Leu Glu Thr
        195                 200                 205

Leu Asn Phe Tyr Leu Thr Asp Ile Ala Val Val Lys Ile Glu Asp Leu
    210                 215                 220

Glu Leu Leu Ala Lys Asn Cys Pro Asn Leu Val Ser Val Lys Leu Thr
```

```
                225                 230                 235                 240

Asp Cys Glu Ile Leu Asp Leu Val Asn Phe Phe Lys His Ala Ser Ala
            245                 250                 255

Leu Glu Glu Phe Cys Gly Gly Thr Tyr Asn Glu Glu Pro Glu Arg Tyr
        260                 265                 270

Ser Ala Ile Ser Leu Pro Ala Lys Leu Cys Arg Leu Gly Leu Thr Tyr
        275                 280                 285

Ile Gly Lys Asn Glu Leu Pro Ile Val Phe Met Phe Ala Ala Val Leu
    290                 295                 300

Lys Lys Leu Asp Leu Leu Tyr Ala Met Leu Asp Thr Glu Asp His Cys
305                 310                 315                 320

Met Leu Ile Gln Arg Cys Pro Asn Leu Glu Val Leu Glu Thr Arg Asn
                325                 330                 335

Val Ile Gly Asp Arg Gly Leu Glu Val Leu Gly Arg Cys Cys Lys Arg
                340                 345                 350

Leu Lys Arg Leu Arg Ile Glu Arg Gly Asp Asp Gln Gly Met Glu
            355                 360                 365

Asp Glu Glu Gly Thr Val Ser His Arg Gly Leu Ile Ala Leu Ser Gln
        370                 375                 380

Gly Cys Ser Glu Leu Glu Tyr Met Ala Val Tyr Val Ser Asp Ile Thr
385                 390                 395                 400

Asn Ala Ser Leu Glu His Ile Gly Thr His Leu Lys Asn Leu Cys Asp
                405                 410                 415

Phe Arg Leu Val Leu Leu Asp His Glu Glu Lys Ile Thr Asp Leu Pro
            420                 425                 430

Leu Asp Asn Gly Val Arg Ala Leu Leu Arg Gly Cys Asp Lys Leu Arg
            435                 440                 445

Arg Phe Ala Leu Tyr Leu Arg Arg Gly Gly Leu Thr Asp Val Gly Leu
        450                 455                 460

Gly Tyr Ile Gly Gln Tyr Ser Pro Asn Val Arg Trp Met Leu Leu Gly
465                 470                 475                 480

Tyr Val Gly Glu Ser Asp Ala Gly Leu Leu Glu Phe Ala Lys Gly Cys
                485                 490                 495

Pro Ser Leu Gln Lys Leu Glu Met Arg Gly Cys Leu Phe Ser Glu
            500                 505                 510

Arg Ala Leu Ala Val Ala Ala Thr Gln Leu Thr Ser Leu Arg Tyr Leu
        515                 520                 525

Trp Val Gln Gly Tyr Gly Val Ser Pro Ser Gly Arg Asp Leu Leu Val
        530                 535                 540

Met Ala Arg Pro Phe Trp Asn Ile Glu Leu Ile Pro Ser Arg Lys Val
545                 550                 555                 560

Ala Thr Asn Thr Asn Pro Asp Glu Thr Val Val Glu His Pro Ala
                565                 570                 575

His Ile Leu Ala Tyr Tyr Ser Leu Ala Gly Gln Arg Ser Asp Phe Pro
            580                 585                 590

Asp Thr Val Val Pro Leu Asp Thr Ala Thr Cys Val Asp Thr
            595                 600                 605

<210> SEQ ID NO 23
<211> LENGTH: 577
<212> TYPE: DNA
<213> ORGANISM: Triticum aestivum
<220> FEATURE:
<221> NAME/KEY: unsure
<222> LOCATION: (296)
```

<223> OTHER INFORMATION: n = A, T, C, or G
<220> FEATURE:
<221> NAME/KEY: unsure
<222> LOCATION: (409)
<223> OTHER INFORMATION: n = A, T, C, or G
<220> FEATURE:
<221> NAME/KEY: unsure
<222> LOCATION: (415)
<223> OTHER INFORMATION: n = A, T, C, or G
<220> FEATURE:
<221> NAME/KEY: unsure
<222> LOCATION: (452)
<223> OTHER INFORMATION: n = A, T, C, or G
<220> FEATURE:
<221> NAME/KEY: unsure
<222> LOCATION: (495)
<223> OTHER INFORMATION: n = A, T, C, or G
<220> FEATURE:
<221> NAME/KEY: unsure
<222> LOCATION: (546)
<223> OTHER INFORMATION: n = A, T, C, or G
<220> FEATURE:
<221> NAME/KEY: unsure
<222> LOCATION: (549)
<223> OTHER INFORMATION: n = A, T, C, or G

<400> SEQUENCE: 23

```
gaactttgtt cctggaagaa tgtataattg ccgatgaagg gagcgaatgg ctccatgaac      60
tcgccgtcaa caattctgtt ctggtgacac tgaacttcta catgacagaa ctcaaagtgg     120
agcctgccga tctggagctt cttgcaagga actgtaaatc attgatttct ctgaagatga     180
gtgactgcga tctttcggat tgattggtt ttctccaaac ctccaaggca ctgcaagaat     240
ccgctgggag gcgcttttttt cgaagtcgga gagtacacca agtacgaaaa ggcaantccc     300
acctagctat gctcctgggg gggcctacct tcatgggtaa aaacgaatcc cgttactttc     360
cgtatccgcg tcgcttaaaa actggacctg catacacttc ctcacaacng aaatnacgtc     420
acttaacgct aaagcccaac ctacgggtct cnagggggc cggtaccaat cgccctatat     480
gatcctatac cgcgncacgg gcgtccttta cactctgacg ggaaactggg taccactaac     540
cctganaanc ccttccactg gtatacaaag gccgacg                              577
```

<210> SEQ ID NO 24
<211> LENGTH: 159
<212> TYPE: PRT
<213> ORGANISM: Triticum aestivum
<220> FEATURE:
<221> NAME/KEY: UNSURE
<222> LOCATION: (98)
<223> OTHER INFORMATION: Xaa = any amino acid
<220> FEATURE:
<221> NAME/KEY: UNSURE
<222> LOCATION: (136)
<223> OTHER INFORMATION: Xaa = any amino acid
<220> FEATURE:
<221> NAME/KEY: UNSURE
<222> LOCATION: (138)
<223> OTHER INFORMATION: Xaa = any amino acid

<400> SEQUENCE: 24

```
Thr Leu Phe Leu Glu Glu Cys Ile Ile Ala Asp Glu Gly Ser Glu Trp
  1               5                  10                  15

Leu His Glu Leu Ala Val Asn Asn Ser Val Leu Val Thr Leu Asn Phe
             20                  25                  30

Tyr Met Thr Glu Leu Lys Val Glu Pro Ala Asp Leu Glu Leu Leu Ala
         35                  40                  45

Arg Asn Cys Lys Ser Leu Ile Ser Leu Lys Met Ser Asp Cys Asp Leu
     50                  55                  60
```

-continued

```
Ser Asp Leu Ile Gly Phe Leu Gln Thr Ser Lys Ala Leu Gln Glu Ser
 65                 70                  75                  80

Ala Gly Arg Arg Phe Phe Arg Ser Arg Arg Val His Gln Val Arg Lys
             85                  90                  95

Gly Xaa Ser His Leu Ala Met Leu Leu Gly Pro Thr Phe Met Gly
        100                 105                 110

Lys Asn Glu Ser Arg Tyr Phe Pro Tyr Pro Arg Arg Leu Lys Thr Gly
            115                 120                 125

Pro Ala Tyr Thr Ser Ser Gln Xaa Lys Xaa Arg His Leu Thr Leu Lys
130                 135                 140

Pro Asn Leu Arg Val Ser Arg Gly Ala Gly Thr Asn Arg Pro Ile
145                 150                 155
```

<210> SEQ ID NO 25
<211> LENGTH: 486
<212> TYPE: DNA
<213> ORGANISM: Triticum aestivum
<220> FEATURE:
<221> NAME/KEY: unsure
<222> LOCATION: (197)
<223> OTHER INFORMATION: n = A, T, C, or G
<220> FEATURE:
<221> NAME/KEY: unsure
<222> LOCATION: (275)
<223> OTHER INFORMATION: n = A, T, C, or G
<220> FEATURE:
<221> NAME/KEY: unsure
<222> LOCATION: (289)
<223> OTHER INFORMATION: n = A, T, C, or G
<220> FEATURE:
<221> NAME/KEY: unsure
<222> LOCATION: (298)
<223> OTHER INFORMATION: n = A, T, C, or G
<220> FEATURE:
<221> NAME/KEY: unsure
<222> LOCATION: (334)
<223> OTHER INFORMATION: n = A, T, C, or G
<220> FEATURE:
<221> NAME/KEY: unsure
<222> LOCATION: (346)
<223> OTHER INFORMATION: n = A, T, C, or G
<220> FEATURE:
<221> NAME/KEY: unsure
<222> LOCATION: (399)
<223> OTHER INFORMATION: n = A, T, C, or G
<220> FEATURE:
<221> NAME/KEY: unsure
<222> LOCATION: (441)
<223> OTHER INFORMATION: n = A, T, C, or G
<220> FEATURE:
<221> NAME/KEY: unsure
<222> LOCATION: (463)
<223> OTHER INFORMATION: n = A, T, C, or G
<220> FEATURE:
<221> NAME/KEY: unsure
<222> LOCATION: (466)
<223> OTHER INFORMATION: n = A, T, C, or G
<220> FEATURE:
<221> NAME/KEY: unsure
<222> LOCATION: (470)
<223> OTHER INFORMATION: n = A, T, C, or G

<400> SEQUENCE: 25

```
cgggaagggg ggaaatcaat ccccatgccc ccaccccctcg ccggaccaga tccccggcgg      60
gccggcgcgg agccttaggc ggggatgggc ggggaggccc cggagccgcg gcggctgagc     120
cgcgcgctca gcctggacgg cggcggcgtc ccggaggagg cgctgcacct ggtgctcggc     180
tacgtggacg acccgcncga ccgcgaggcg gcctcgctgg cgtgccgccg ctggcaccac     240
```

```
atcgacgcgc tcacgcggaa gcacgtcacc gtgcncttct gctacgccng tgtccccngc    300
gcgcctgctc gcgcgcttcc cgcgcctcga gtcnctcggg gtcaaggca agcccgcgcc    360 gccatgtacg gctcatcccc gacgactggg gcgcctacnc ccgggccctg cgtccctgag    420
ctcgccgccc cgctcgattg nctcaaggcg gctcaaccTt gcnccncaan gtcgtcaccg    480
acgaca                                                              486
```

<210> SEQ ID NO 26
<211> LENGTH: 134
<212> TYPE: PRT
<213> ORGANISM: Triticum aestivum
<220> FEATURE:
<221> NAME/KEY: UNSURE
<222> LOCATION: (38)
<223> OTHER INFORMATION: Xaa = any amino acid
<220> FEATURE:
<221> NAME/KEY: UNSURE
<222> LOCATION: (64)
<223> OTHER INFORMATION: Xaa = any amino acid
<220> FEATURE:
<221> NAME/KEY: UNSURE
<222> LOCATION: (69)
<223> OTHER INFORMATION: Xaa = any amino acid
<220> FEATURE:
<221> NAME/KEY: UNSURE
<222> LOCATION: (72)
<223> OTHER INFORMATION: Xaa = any amino acid
<220> FEATURE:
<221> NAME/KEY: UNSURE
<222> LOCATION: (84)
<223> OTHER INFORMATION: Xaa = any amino acid
<220> FEATURE:
<221> NAME/KEY: UNSURE
<222> LOCATION: (88)
<223> OTHER INFORMATION: Xaa = any amino acid
<220> FEATURE:
<221> NAME/KEY: UNSURE
<222> LOCATION: (119)
<223> OTHER INFORMATION: Xaa = any amino acid
<220> FEATURE:
<221> NAME/KEY: UNSURE
<222> LOCATION: (127)..(128)..(129)
<223> OTHER INFORMATION: Xaa = any amino acid

<400> SEQUENCE: 26

Met Gly Gly Glu Ala Pro Glu Pro Arg Arg Leu Ser Arg Ala Leu Ser
 1               5                  10                  15

Leu Asp Gly Gly Gly Val Pro Glu Glu Ala Leu His Leu Val Leu Gly
                20                  25                  30

Tyr Val Asp Asp Pro Xaa Asp Arg Glu Ala Ala Ser Leu Ala Cys Arg
            35                  40                  45

Arg Trp His His Ile Asp Ala Leu Thr Arg Lys His Val Thr Val Xaa
     50                  55                  60

Phe Cys Tyr Ala Xaa Val Pro Xaa Ala Pro Arg Ala Leu Pro Ala
 65                  70                  75                  80

Pro Arg Val Xaa Arg Gly Gln Xaa Gln Ala Arg Ala Met Tyr Gly
                 85                  90                  95

Ser Ser Pro Thr Thr Gly Ala Pro Thr Pro Gly Pro Cys Val Pro Glu
            100                 105                 110

Leu Ala Ala Pro Leu Asp Xaa Leu Lys Ala Ala Gln Pro Cys Xaa Xaa
        115                 120                 125

Xaa Ser Ser Pro Thr Thr
    130

<210> SEQ ID NO 27

<211> LENGTH: 1074
<212> TYPE: DNA
<213> ORGANISM: Triticum aestivum

<400> SEQUENCE: 27

```
gcacgaggta ggattgatgg ctgtagctga aggctgtcct gatttggagt actgggcagt    60
acatgtgtct gacattacaa atgcagctct tgaggctatt ggcgcattca gcaaaaacct   120
gaacgatttc cgacttgtcc tgcttgatag agaggtgcat ataactgaac tgccccttga   180
caacggggtt cgggctttgc tgagaggttg caccaaactc cggaggtttg cattttatgt   240
gagacctgga gctctatcag atattggcct ttcttatgtt ggcgaattta caagaccgt    300
ccgctacatg ttgcttggga atgccggggg gtctgatgat ggactgctgg catttgcacg   360
aggatgccca agcttgcaga aattggagct aaggagttgc tgctttagtg aacgtgcatt   420
ggcagttgca gccttacagc tgaagtcact cagatatctt gggtgcagg gatacaaggc   480
atctcctact ggcaccgatc tcatggcaat ggtacgcccc ttctggaaca ttgagtttat   540
tgcaccaaat caagatgagc cttgcccaga gggtcaggca cagattctgg catactactc   600
tctggctggg gcaaggacag attgtcctca gtcagtaatt cccctccatc cgtcagtggg   660
aagctaaaaa gaccaccacc agtttgactg tacatacatg tttgatgcca gcaaaaccca   720
caatgcggta tagggacatt ccaccttaca gtgccaatta cgggactgaa agctcaagta   780
aaagcgaccc actctgaact gccttggtat cttaggggca acattttggg gtaagctgtt   840
catctggcca acatggatat ctttgtgtac tacaccattt tgacatggct cggacacgca   900
tttttgtaat aatgtgccca gttgtaatgg cattttttctg ttcttgagct ttgcccactg   960
tattgttgtt ctacaaacag tattggatta gttgttgtac catctgtgaa acaatctgca  1020
caatgttatg tttaacccat gaatatcttg aaaaaaaaaa aaaaaaaaaa aaaa         1074
```

<210> SEQ ID NO 28
<211> LENGTH: 221
<212> TYPE: PRT
<213> ORGANISM: Triticum aestivum

<400> SEQUENCE: 28

```
His Glu Val Gly Leu Met Ala Val Ala Glu Gly Cys Pro Asp Leu Glu
  1               5                  10                  15

Tyr Trp Ala Val His Val Ser Asp Ile Thr Asn Ala Ala Leu Glu Ala
             20                  25                  30

Ile Gly Ala Phe Ser Lys Asn Leu Asn Asp Phe Arg Leu Val Leu Leu
         35                  40                  45

Asp Arg Glu Val His Ile Thr Glu Leu Pro Leu Asp Asn Gly Val Arg
     50                  55                  60

Ala Leu Leu Arg Gly Cys Thr Lys Leu Arg Arg Phe Ala Phe Tyr Val
 65                  70                  75                  80

Arg Pro Gly Ala Leu Ser Asp Ile Gly Leu Ser Tyr Val Gly Glu Phe
                 85                  90                  95

Ser Lys Thr Val Arg Tyr Met Leu Leu Gly Asn Ala Gly Gly Ser Asp
            100                 105                 110

Asp Gly Leu Leu Ala Phe Ala Arg Gly Cys Pro Ser Leu Gln Lys Leu
        115                 120                 125

Glu Leu Arg Ser Cys Cys Phe Ser Glu Arg Ala Leu Ala Val Ala Ala
    130                 135                 140

Leu Gln Leu Lys Ser Leu Arg Tyr Leu Trp Val Gln Gly Tyr Lys Ala
145                 150                 155                 160
```

```
Ser Pro Thr Gly Thr Asp Leu Met Ala Met Val Arg Pro Phe Trp Asn
            165                 170                 175

Ile Glu Phe Ile Ala Pro Asn Gln Asp Glu Pro Cys Pro Glu Gly Gln
        180                 185                 190

Ala Gln Ile Leu Ala Tyr Tyr Ser Leu Ala Gly Ala Arg Thr Asp Cys
    195                 200                 205

Pro Gln Ser Val Ile Pro Leu His Pro Ser Val Gly Ser
    210                 215                 220

<210> SEQ ID NO 29
<211> LENGTH: 1812
<212> TYPE: DNA
<213> ORGANISM: Oryza sativa
<220> FEATURE:
<221> NAME/KEY: unsure
<222> LOCATION: (1108)
<223> OTHER INFORMATION: n = A, T, C, or G

<400> SEQUENCE: 29
```

| | | | | | |
|---|---|---|---|---|---|
| cccccgggct | gcaggaattc | ggcacgaggt | cacgcaacca | cggactcctc | ctccacctcc | 60 |
| gtttcctact | ctcttcttca | gtttctcacc | tctccgcacg | agaaaattcg | aatccccctt | 120 |
| ccggctgctg | gttttcgtgc | cagaaacagg | cgattttacc | agtgccagtt | agctctcgcc | 180 |
| ttcctcctcc | tccatcgtgc | tactactctg | ttcttctgga | agaacactgg | tctcctcgcc | 240 |
| tacctcagtc | accactcacc | acaccaggtg | cgagctataa | aaaccggcac | gccaaaaatc | 300 |
| ttcaaaacca | cacagaaacc | tcagatctcc | gaggcttcca | agcgagtcga | cgaaaatgcc | 360 |
| cgtgatggct | ccgaccgcat | ctcttctcct | ctccccgagg | ccgctgccgg | cgagccgccg | 420 |
| ggtcccctcg | ctcccggcgc | tctcggcttc | cgtcgcctg | cgcctccgcc | gcgcccgcgc | 480 |
| cgacacacgg | ctccgcgtgg | cggcgccgcc | gtccgtcccc | ggggaggcgg | accaggcgcc | 540 |
| cggggagacc | gagccgagca | cgtcgtcggc | cgacgagaag | ttcgtgtgga | gggaccactg | 600 |
| gtaccccgtg | tccctcgtcg | aggacctcga | ccccagcgtg | cccaccccgt | tccagctcct | 660 |
| caaccgcgac | ctcgtcatct | ggaaggaccc | aaaatccggc | gagtgggtcg | ccctcgacga | 720 |
| ccgttgcccc | catcgcctcg | cgcccctctc | ggaggggcgg | atcgatgaga | cggggtgctt | 780 |
| gcagtgctca | taccacggct | ggtcattcga | tggctccggc | gcgtgcaccc | ggatcccgca | 840 |
| ggcggcgccc | gaggggccgg | aggccaaggc | tgtgaggtcg | ccgaaggcgt | gcgcgatcaa | 900 |
| gttccccacc | ctcgtctcgc | aagggctgct | cttcgtgtgg | cccgacgaga | atgggtggga | 960 |
| gaaggccacg | gctaccaagc | tccgatgtt | accgaaggag | tttgaggatc | ctgcgttctc | 1020 |
| cacggtgacc | atccagaggg | atctgtacta | tggctatgat | acattgatgg | agaacgtctc | 1080 |
| tgatccgtcg | catatagaat | tgctcanca | caaggtcact | ggtcgaagag | atcgagccag | 1140 |
| gcctttgcca | ttcaagatgg | aatcaagtgg | tgcatgggga | tattcagggt | caaattctgg | 1200 |
| aaaccctcgc | atcagtgcaa | cttttgtggc | cccttgctat | gcactgaaca | aaattgagat | 1260 |
| agacacaaag | ttacccattt | ttggagatca | gaaatgggtc | atatggattt | gctcttcaa | 1320 |
| cattccaatg | gccccaggga | agactcgttc | tatagtttgt | agtgctcgga | acttttccaa | 1380 |
| gtttagcatg | ccaggaaaag | catggtggca | gcttgtccct | cgatggtatg | agcattggac | 1440 |
| ttcaaatttg | gtctatgatg | gtgatatgat | agttctgcaa | gggcaagaga | agattttctt | 1500 |
| gtctgcatcg | aaggagtctt | ctgcagatat | taatcagcag | tacacaaaga | tcacgtttac | 1560 |
| acccacgcag | gctgaccgtt | tgttttggc | attccgggca | tggctaagga | aatttggtaa | 1620 |

```
cagccaacct gactggtttg gaaatcctag ccaagaagtg ttgccttcca ctgtcctttc    1680
aaagcgtgag atgctagata gatatgagca gcacacactg aaatgctcat cttgcaaagg    1740
ggcatacaac gccttccaga ctctgcaaaa ggtcttcatg ggagcgacag tggccgttct    1800
attattgctt gc                                                        1812
```

<210> SEQ ID NO 30
<211> LENGTH: 485
<212> TYPE: PRT
<213> ORGANISM: Oryza sativa
<220> FEATURE:
<221> NAME/KEY: UNSURE
<222> LOCATION: (251)
<223> OTHER INFORMATION: Xaa = any amino acid

<400> SEQUENCE: 30

```
Met Pro Val Met Ala Pro Thr Ala Ser Leu Leu Ser Pro Arg Pro
 1               5                  10                  15

Leu Pro Ala Ser Arg Arg Val Pro Ser Leu Pro Ala Leu Ser Ala Ser
                20                  25                  30

Gly Arg Leu Arg Leu Arg Arg Ala Arg Ala Asp Thr Arg Leu Arg Val
        35                  40                  45

Ala Ala Pro Pro Ser Val Pro Gly Glu Ala Asp Gln Ala Pro Gly Glu
    50                  55                  60

Thr Glu Pro Ser Thr Ser Ser Ala Asp Glu Lys Phe Val Trp Arg Asp
65                  70                  75                  80

His Trp Tyr Pro Val Ser Leu Val Glu Asp Leu Asp Pro Ser Val Pro
                85                  90                  95

Thr Pro Phe Gln Leu Leu Asn Arg Asp Leu Val Ile Trp Lys Asp Pro
            100                 105                 110

Lys Ser Gly Glu Trp Val Ala Leu Asp Asp Arg Cys Pro His Arg Leu
        115                 120                 125

Ala Pro Leu Ser Glu Gly Arg Ile Asp Glu Thr Gly Cys Leu Gln Cys
    130                 135                 140

Ser Tyr His Gly Trp Ser Phe Asp Gly Ser Gly Ala Cys Thr Arg Ile
145                 150                 155                 160

Pro Gln Ala Ala Pro Glu Gly Pro Glu Ala Lys Ala Val Arg Ser Pro
                165                 170                 175

Lys Ala Cys Ala Ile Lys Phe Pro Thr Leu Val Ser Gln Gly Leu Leu
            180                 185                 190

Phe Val Trp Pro Asp Glu Asn Gly Trp Glu Lys Ala Thr Ala Thr Lys
        195                 200                 205

Pro Pro Met Leu Pro Lys Glu Phe Glu Asp Pro Ala Phe Ser Thr Val
    210                 215                 220

Thr Ile Gln Arg Asp Leu Tyr Tyr Gly Tyr Asp Thr Leu Met Glu Asn
225                 230                 235                 240

Val Ser Asp Pro Ser His Ile Glu Phe Ala Xaa His Lys Val Thr Gly
                245                 250                 255

Arg Arg Asp Arg Ala Arg Pro Leu Pro Phe Lys Met Glu Ser Ser Gly
            260                 265                 270

Ala Trp Gly Tyr Ser Gly Ser Asn Ser Gly Asn Pro Arg Ile Ser Ala
        275                 280                 285

Thr Phe Val Ala Pro Cys Tyr Ala Leu Asn Lys Ile Glu Ile Asp Thr
    290                 295                 300

Lys Leu Pro Ile Phe Gly Asp Gln Lys Trp Val Ile Trp Ile Cys Ser
305                 310                 315                 320
```

```
Phe Asn Ile Pro Met Ala Pro Gly Lys Thr Arg Ser Ile Val Cys Ser
                325                 330                 335

Ala Arg Asn Phe Phe Gln Phe Ser Met Pro Gly Lys Ala Trp Trp Gln
            340                 345                 350

Leu Val Pro Arg Trp Tyr Glu His Trp Thr Ser Asn Leu Val Tyr Asp
        355                 360                 365

Gly Asp Met Ile Val Leu Gln Gly Gln Glu Lys Ile Phe Leu Ser Ala
    370                 375                 380

Ser Lys Glu Ser Ser Ala Asp Ile Asn Gln Gln Tyr Thr Lys Ile Thr
385                 390                 395                 400

Phe Thr Pro Thr Gln Ala Asp Arg Phe Val Leu Ala Phe Arg Ala Trp
                405                 410                 415

Leu Arg Lys Phe Gly Asn Ser Gln Pro Asp Trp Phe Gly Asn Pro Ser
            420                 425                 430

Gln Glu Val Leu Pro Ser Thr Val Leu Ser Lys Arg Glu Met Leu Asp
        435                 440                 445

Arg Tyr Glu Gln His Thr Leu Lys Cys Ser Ser Cys Lys Gly Ala Tyr
    450                 455                 460

Asn Ala Phe Gln Thr Leu Gln Lys Val Phe Met Gly Ala Thr Val Ala
465                 470                 475                 480

Val Leu Leu Leu Leu
                485

<210> SEQ ID NO 31
<211> LENGTH: 1930
<212> TYPE: DNA
<213> ORGANISM: Glycine max

<400> SEQUENCE: 31
gggaagaaag aaacatttga aacttgcacg actcaactac aatctctctt atgaacacat      60
ctcatttgaa cctctataaa caaattttca aaccttaaca ccttacgaaa atcaactaaa     120
gaaaaccatt gatggcgctc cctcactcca tctctgcctt agccaccaca ctcacactct     180
cctccccaat aaccaaaccc cataaagtta accccttttcc cttttcctcg aaccgaaatt     240
cacaattttt aacgaaacaa acgcgaccca gaagcagaag aaacctctcc ctaaccctg     300 cacgcgttgc ggcgccaccc tcaacggttg aagccgatcg attataccca gaggccgaaa     360
ataacgaaac tgaggaagag tttagcgacg agagctcttc ctctaaattc acttggaggg     420
atcactggta ccctgtctcg ttaattgaag atctgaaccc tctcttgccc acaccgtttc     480
agcttctggg tcgtgaaatc gtgctctggt acgacaagtc catttcccaa tgggttgctt     540
ttgatgacaa atgcccccat cgtcttgccc ctttatctga aggaggata gatgaagatg     600 ggaagttgca gtgttcttat catgggtggt cttttgatgg gtgtggatct tgtgttaaga     660
ttcctcaggc ttcatctgaa ggccccgaag cacgtgctat tggatctcct aaagcatgtg     720
ccactaggtt ccctaccttg gtgtcccagg gtttgctctt gtatgggct gatgagaatg     780 gttgggagaa agcaaaggcc tccaaccctc caatgtttcc tgatgacttt gacaaaccgg     840
agtttcccac ggtcaacata cagcgtgatt tgttctatgg ttacgatact cttatggaga     900
atgtctctga tccttctcac attgagtttg ctcatcacaa ggtcacggga aggagagaca     960
gagccaaacc tctgccattc aagatggatt ctcgtggttc atggggcttc tctggagcta    1020
atgaagggaa cccacagatc agtgccaagt tgttgcacc atgttatatg atgaacaaga    1080
ttgagattga taccaaactc cctgtagttg gtgaccagaa atgggtagta tggatatgtt    1140
```

-continued

```
ccttcaatgt ccccatggca cctggtaaga ctcgctccat tgtttgcagt gctcgaaact    1200
tcttccagtt ctcagtgcca gggcctgcct ggtggcaagt caactgagta atcttactgt    1260
ttgcattcaa ttttaaacaa tgcatacatg taactcaggt cgttcctaga tggtatgagc    1320
attggacttc aaataaggta tatgatggag acatgattgt ccttcaaggt caagagaaaa    1380
tcttcctttc agaaaccaag gaaggtggtg acattaacaa acagtacaca acatcaccct    1440
tcacaccaac acaggcagat cgctttgtct tggcattccg aaattggctg aggcgacatg    1500
gcaatggcca accagaatgg tttggaaaca gcagcgacca gccattgcca tcaactgtgt    1560
tatcaaaacg tcagatgttg atagatttg aacagcacac tctcaagtgt tcatcatgta    1620
aagcagcata tgagggattc caaacatggc agaaagtcct aattgggca acagttgtgt    1680 tttgtgcaac atcagggatc ccatcagatt ccagttgcg tgtacttttg gctggactcg    1740
cagttgtcag cgcagccata gcttttgccc taaaccaact ccaaaagaat tttgaattcg    1800
tggattacgt gcatgcggaa atcgattaag cacgtccctc caaggaact tcaactagtt    1860 agttgtaaat agagttgaag acaagtacat gtacactagt attttgatga aaagagctca    1920
aatctacctt                                                           1930
```

<210> SEQ ID NO 32
<211> LENGTH: 563
<212> TYPE: PRT
<213> ORGANISM: Glycine max

<400> SEQUENCE: 32

```
Met Ala Leu Pro His Ser Ile Ser Ala Leu Ala Thr Thr Leu Thr Leu
 1               5                  10                  15

Ser Ser Pro Ile Thr Lys Pro His Lys Val Asn Pro Phe Pro Phe Ser
                20                  25                  30

Ser Asn Arg Asn Ser Gln Phe Leu Thr Lys Gln Thr Arg Pro Arg Ser
            35                  40                  45

Arg Arg Asn Leu Ser Leu Thr Pro Ala Arg Val Ala Ala Pro Pro Ser
        50                  55                  60

Thr Val Glu Ala Asp Arg Leu Tyr Pro Glu Ala Glu Asn Asn Glu Thr
65                  70                  75                  80

Glu Glu Glu Phe Ser Asp Glu Ser Ser Lys Phe Thr Trp Arg Asp
                85                  90                  95

His Trp Tyr Pro Val Ser Leu Ile Glu Asp Leu Asn Pro Leu Leu Pro
                100                 105                 110

Thr Pro Phe Gln Leu Leu Gly Arg Glu Ile Val Leu Trp Tyr Asp Lys
            115                 120                 125

Ser Ile Ser Gln Trp Val Ala Phe Asp Asp Lys Cys Pro His Arg Leu
        130                 135                 140

Ala Pro Leu Ser Glu Gly Arg Ile Asp Glu Asp Gly Lys Leu Gln Cys
145                 150                 155                 160

Ser Tyr His Gly Trp Ser Phe Asp Gly Cys Gly Ser Cys Val Lys Ile
                165                 170                 175

Pro Gln Ala Ser Ser Glu Gly Pro Glu Ala Arg Ala Ile Gly Ser Pro
            180                 185                 190

Lys Ala Cys Ala Thr Arg Phe Pro Thr Leu Val Ser Gln Gly Leu Leu
        195                 200                 205

Phe Val Trp Ala Asp Glu Asn Gly Trp Glu Lys Ala Lys Ala Ser Asn
    210                 215                 220
```

-continued

```
Pro Pro Met Phe Pro Asp Asp Phe Asp Lys Pro Glu Phe Pro Thr Val
225                 230                 235                 240

Asn Ile Gln Arg Asp Leu Phe Tyr Gly Tyr Asp Thr Leu Met Glu Asn
            245                 250                 255

Val Ser Asp Pro Ser His Ile Glu Phe Ala His His Lys Val Thr Gly
        260                 265                 270

Arg Arg Asp Arg Ala Lys Pro Leu Pro Phe Lys Met Asp Ser Arg Gly
    275                 280                 285

Ser Trp Gly Phe Ser Gly Ala Asn Glu Gly Asn Pro Gln Ile Ser Ala
290                 295                 300

Lys Phe Val Ala Pro Cys Tyr Met Met Asn Lys Ile Glu Ile Asp Thr
305                 310                 315                 320

Lys Leu Pro Val Val Gly Asp Gln Lys Trp Val Val Trp Ile Cys Ser
                325                 330                 335

Phe Asn Val Pro Met Ala Pro Gly Lys Thr Arg Ser Ile Val Cys Ser
            340                 345                 350

Ala Arg Asn Phe Phe Gln Phe Ser Val Pro Gly Pro Ala Trp Trp Gln
        355                 360                 365

Val Asn Val Ile Leu Leu Phe Ala Phe Asn Phe Lys Gln Cys Ile His
370                 375                 380

Val Thr Gln Val Val Pro Arg Trp Tyr Glu His Trp Thr Ser Asn Lys
385                 390                 395                 400

Val Tyr Asp Gly Asp Met Ile Val Leu Gln Gly Gln Glu Lys Ile Phe
                405                 410                 415

Leu Ser Glu Thr Lys Glu Gly Gly Asp Ile Asn Lys Gln Tyr Thr Asn
            420                 425                 430

Ile Thr Phe Thr Pro Thr Gln Ala Asp Arg Phe Val Leu Ala Phe Arg
        435                 440                 445

Asn Trp Leu Arg Arg His Gly Asn Gly Gln Pro Glu Trp Phe Gly Asn
    450                 455                 460

Ser Ser Asp Gln Pro Leu Pro Ser Thr Val Leu Ser Lys Arg Gln Met
465                 470                 475                 480

Leu Asp Arg Phe Glu Gln His Thr Leu Lys Cys Ser Ser Cys Lys Ala
                485                 490                 495

Ala Tyr Glu Gly Phe Gln Thr Trp Gln Lys Val Leu Ile Gly Ala Thr
            500                 505                 510

Val Val Phe Cys Ala Thr Ser Gly Ile Pro Ser Asp Phe Gln Leu Arg
        515                 520                 525

Val Leu Leu Ala Gly Leu Ala Val Val Ser Ala Ala Ile Ala Phe Ala
    530                 535                 540

Leu Asn Gln Leu Gln Lys Asn Phe Glu Phe Val Asp Tyr Val His Ala
545                 550                 555                 560

Glu Ile Asp

<210> SEQ ID NO 33
<211> LENGTH: 555
<212> TYPE: DNA
<213> ORGANISM: Triticum aestivum
<220> FEATURE:
<221> NAME/KEY: unsure
<222> LOCATION: (228)
<223> OTHER INFORMATION: n = A, T, C, or G
<220> FEATURE:
<221> NAME/KEY: unsure
<222> LOCATION: (252)
<223> OTHER INFORMATION: n = A, T, C, or G
<220> FEATURE:
```

```
<221> NAME/KEY: unsure
<222> LOCATION: (354)
<223> OTHER INFORMATION: n = A, T, C, or G
<220> FEATURE:
<221> NAME/KEY: unsure
<222> LOCATION: (369)
<223> OTHER INFORMATION: n = A, T, C, or G
<220> FEATURE:
<221> NAME/KEY: unsure
<222> LOCATION: (402)
<223> OTHER INFORMATION: n = A, T, C, or G
<220> FEATURE:
<221> NAME/KEY: unsure
<222> LOCATION: (412)
<223> OTHER INFORMATION: n = A, T, C, or G
<220> FEATURE:
<221> NAME/KEY: unsure
<222> LOCATION: (415)
<223> OTHER INFORMATION: n = A, T, C, or G
<220> FEATURE:
<221> NAME/KEY: unsure
<222> LOCATION: (441)
<223> OTHER INFORMATION: n = A, T, C, or G
<220> FEATURE:
<221> NAME/KEY: unsure
<222> LOCATION: (460)
<223> OTHER INFORMATION: n = A, T, C, or G
<220> FEATURE:
<221> NAME/KEY: unsure
<222> LOCATION: (467)
<223> OTHER INFORMATION: n = A, T, C, or G
<220> FEATURE:
<221> NAME/KEY: unsure
<222> LOCATION: (482)
<223> OTHER INFORMATION: n = A, T, C, or G
<220> FEATURE:
<221> NAME/KEY: unsure
<222> LOCATION: (504)
<223> OTHER INFORMATION: n = A, T, C, or G
<220> FEATURE:
<221> NAME/KEY: unsure
<222> LOCATION: (506)
<223> OTHER INFORMATION: n = A, T, C, or G
<220> FEATURE:
<221> NAME/KEY: unsure
<222> LOCATION: (519)..(520)
<223> OTHER INFORMATION: n = A, T, C, or G
<220> FEATURE:
<221> NAME/KEY: unsure
<222> LOCATION: (524)
<223> OTHER INFORMATION: n = A, T, C, or G
<220> FEATURE:
<221> NAME/KEY: unsure
<222> LOCATION: (539)
<223> OTHER INFORMATION: n = A, T, C, or G
<220> FEATURE:
<221> NAME/KEY: unsure
<222> LOCATION: (541)
<223> OTHER INFORMATION: n = A, T, C, or G
<220> FEATURE:
<221> NAME/KEY: unsure
<222> LOCATION: (544)
<223> OTHER INFORMATION: n = A, T, C, or G
<220> FEATURE:
<221> NAME/KEY: unsure
<222> LOCATION: (555)
<223> OTHER INFORMATION: n = A, T, C, or G

<400> SEQUENCE: 33
tccacccacg ccgtcgatca cccggtggtc accaccggcg acatggatcc cctccgccta      60
ctcctccccc gcgcccaggc ccagcccttg cttccgctcc ccaccggcgt ccaagcaccg     120
agcgtcaggc cccaactcgt cccgcggcga cgggcgcgcc gccaccgcaa cggggccgcg     180
cggatgctgc cggcctcggc cgtggcgtcc gagtcgccgt ggacgganca ggagccgcca     240
tccggggaga angaggagcg gttcgactgg ctggaccagt ggtaccccct cgcccccgtg     300
```

```
gaggacctgg acccggcgcg cccacggcaa atggtgctgg gatccgcgtg gtanctggta    360
caacgcggng ccggcgaatg gcgctgttca caccgtgccc gnacgcctgg cncgnctcga    420
gggcgcatca caaaaggcgg ncagtcgtta cacgggtggn ctcacgncgc gggctgaatt    480
ancccaggcc cgcctcggca acgngnaaca aaacagggnn gtgnttaacc gtctgtgana    540
naanttgtgt ctccn                                                    555
```

```
<210> SEQ ID NO 34
<211> LENGTH: 144
<212> TYPE: PRT
<213> ORGANISM: Triticum aestivum
<220> FEATURE:
<221> NAME/KEY: UNSURE
<222> LOCATION: (62)
<223> OTHER INFORMATION: Xaa = any amino acid
<220> FEATURE:
<221> NAME/KEY: UNSURE
<222> LOCATION: (70)
<223> OTHER INFORMATION: Xaa = any amino acid
<220> FEATURE:
<221> NAME/KEY: UNSURE
<222> LOCATION: (104)
<223> OTHER INFORMATION: Xaa = any amino acid
<220> FEATURE:
<221> NAME/KEY: UNSURE
<222> LOCATION: (124)..(125)
<223> OTHER INFORMATION: Xaa = any amino acid
<220> FEATURE:
<221> NAME/KEY: UNSURE
<222> LOCATION: (140)
<223> OTHER INFORMATION: Xaa = any amino acid
<220> FEATURE:
<221> NAME/KEY: UNSURE
<222> LOCATION: (142)
<223> OTHER INFORMATION: Xaa = any amino acid

<400> SEQUENCE: 34

Met Asp Pro Leu Arg Leu Leu Pro Arg Ala Gln Ala Gln Pro Leu
 1               5                  10                  15

Leu Pro Leu Pro Thr Gly Val Gln Ala Pro Ser Val Arg Pro Gln Leu
                20                  25                  30

Val Pro Arg Arg Arg Ala Arg Arg His Arg Asn Gly Ala Ala Arg Met
            35                  40                  45

Leu Pro Ala Ser Ala Val Ala Ser Glu Ser Pro Trp Thr Xaa Gln Glu
        50                  55                  60

Pro Pro Ser Gly Glu Xaa Glu Glu Arg Phe Asp Trp Leu Asp Gln Trp
 65                  70                  75                  80

Tyr Pro Phe Ala Pro Val Glu Asp Leu Asp Pro Ala Arg Pro Arg Gln
                85                  90                  95

Met Val Leu Gly Ser Ala Trp Xaa Leu Val Gln Arg Gly Ala Gly Glu
           100                 105                 110

Trp Arg Cys Ser His Arg Ala Arg Thr Pro Gly Xaa Xaa Arg Gly Arg
       115                 120                 125

Ile Thr Lys Gly Gly Gln Ser Leu His Gly Trp Xaa His Xaa Ala Gly
   130                 135                 140

<210> SEQ ID NO 35
<211> LENGTH: 1864
<212> TYPE: DNA
<213> ORGANISM: Triticum aestivum

<400> SEQUENCE: 35
gcacgagggc aatgttctag aagcaccgaa gcaccgagag ataagtggca ctagtacaaa    60
```

-continued

```
gctggagcga ggaagatctc ggccccaaca aaacctcgga ccccttccct ccacacgatc    120
ccgaggaagg aaggaaaggc agacgaaatg ccggtgctgg cgatgccgtc cgcctccctc    180
cccctcctct cccccggggc accggccgct gctgcgcccg tcgaccctcc cggcctcccg    240
tctcggcagc ggcatcctcc gcgtggccgc gccgacgtcg gtccccggcg aggcggagcg    300
ggcggaggag ccgagcacga gcacgagcac ctcgcctgaa tcgtccgggg agaagttcgt    360
gtggcgggac cactggtacc cggtctcgct cgtggaggac ctggacccgc gcgtgcccac    420
cccgttccag ctcctcaacc gcgacctcgt catctggaac gacccccaact ccggcgactg    480 ggtcgcgctc gacgaccgct gcccgcaccg cctcgccccg ctctcggagg ggcggatcga    540
cgagacgggc ggcctgcagt gctcctacca cggctggtcc ttcgacggct ccggcgcctg    600
caccaggatc ccgcaggccg cgcccgaggg gcccgaggcc cgggcggtgc gctcgcccag    660
ggcctgcgcc accaagttcc ccaccctcct ctcccagggc ctgctcttcg tctggcctga    720
cgagaatgga tgggacaagg ccaaggccac caagcctcca atgctgccga aggagttcga    780
tgacccggcc ttctccaccg tgacgatcca gagggacctc ttctatgggt atgcacgtt    840 gatggagaac gtctctgatc cctcgcatat agaatttgct caccacaagg tcactggacg    900
aagagataga gccaagcctt tgccatttaa aatggaatca agtggcgcat ggggatattc    960 agggggcaaat accggcaatc ctcgcatcac tgcaactttc gaggcccctt gctatgcact   1020
gaacaaaata gagattgaca ccaaattacc gattgtggga gatcagaaat gggtcatatg   1080
gatttgctcc ttcaacattc caatggcccc agggaaaact cgttctattg tctgtagtgc   1140
tcgaaacttt ttccagttta caatgccagg aaaggcatgg tggcagtttg tccctcgatg   1200
gtacgaacat tggacctcaa atttggtcta cgacggcgat atgatcgtgc ttcaaggcca   1260
agagaaggtt ttcctgtctg catccaagga gtcgtctgca gatgttaatc agcagtacac   1320
aaagctcaca ttcacaccca cacaggccga ccgatttgtt ttagcattcc gggcatggct   1380
acgaaaattc ggaaatagcc agcctgactg gtatggaagt cctagccaag atgcattgcc   1440
ttctacggtc ctttcaaagc gagagatgct agacagatac gagcagcaca cgctgaaatg   1500
ctcgtcctgc agaggagcgc acaaggcctt tcagactttg cagaaggtgt tcatgggggc   1560
gacggtggtg tttggcgcga catccgggat ccctgcggat gttcagctca gaatattgct   1620
cggtgccggt gctctggtca gcgccgctct ggcctatgtc ttctacgacc gccagaagca   1680
tttcgtgttt gtggactacg tgcacgctga cattgattga ttagggagat aaacattagt   1740 tattttttgtg aggatctggt gtggtgtggt gtggagacat cccacgatca atcatgtgca   1800
taacctagcc aaggagtaca tatagctttc agtgggtaca tgagattggc ccagtatgtt   1860
gttt                                                                1864
```

<210> SEQ ID NO 36
<211> LENGTH: 487
<212> TYPE: PRT
<213> ORGANISM: Triticum aestivum

<400> SEQUENCE: 36

```
Leu Arg Val Ala Ala Pro Thr Ser Val Pro Gly Glu Ala Glu Arg Ala
 1               5                  10                  15

Glu Glu Pro Ser Thr Ser Thr Ser Thr Ser Pro Glu Ser Ser Gly Glu
            20                  25                  30

Lys Phe Val Trp Arg Asp His Trp Tyr Pro Val Ser Leu Val Glu Asp
        35                  40                  45
```

```
Leu Asp Pro Arg Val Pro Thr Pro Phe Gln Leu Leu Asn Arg Asp Leu
     50                  55                  60

Val Ile Trp Asn Asp Pro Asn Ser Gly Asp Trp Val Ala Leu Asp Asp
 65                  70                  75                  80

Arg Cys Pro His Arg Leu Ala Pro Leu Ser Glu Gly Arg Ile Asp Glu
                 85                  90                  95

Thr Gly Leu Gln Cys Ser Tyr His Gly Trp Ser Phe Asp Gly Ser
            100                 105                 110

Gly Ala Cys Thr Arg Ile Pro Gln Ala Ala Pro Glu Gly Pro Glu Ala
             115                 120                 125

Arg Ala Val Arg Ser Pro Arg Ala Cys Ala Thr Lys Phe Pro Thr Leu
     130                 135                 140

Leu Ser Gln Gly Leu Leu Phe Val Trp Pro Asp Glu Asn Gly Trp Asp
145                 150                 155                 160

Lys Ala Lys Ala Thr Lys Pro Pro Met Leu Pro Lys Glu Phe Asp Asp
                 165                 170                 175

Pro Ala Phe Ser Thr Val Thr Ile Gln Arg Asp Leu Phe Tyr Gly Tyr
             180                 185                 190

Asp Thr Leu Met Glu Asn Val Ser Asp Pro Ser His Ile Glu Phe Ala
     195                 200                 205

His His Lys Val Thr Gly Arg Arg Asp Arg Ala Lys Pro Leu Pro Phe
     210                 215                 220

Lys Met Glu Ser Ser Gly Ala Trp Gly Tyr Ser Gly Ala Asn Thr Gly
225                 230                 235                 240

Asn Pro Arg Ile Thr Ala Thr Phe Glu Ala Pro Cys Tyr Ala Leu Asn
             245                 250                 255

Lys Ile Glu Ile Asp Thr Lys Leu Pro Ile Val Gly Asp Gln Lys Trp
             260                 265                 270

Val Ile Trp Ile Cys Ser Phe Asn Ile Pro Met Ala Pro Gly Lys Thr
     275                 280                 285

Arg Ser Ile Val Cys Ser Ala Arg Asn Phe Phe Gln Phe Thr Met Pro
     290                 295                 300

Gly Lys Ala Trp Trp Gln Phe Val Pro Arg Trp Tyr Glu His Trp Thr
305                 310                 315                 320

Ser Asn Leu Val Tyr Asp Gly Asp Met Ile Val Leu Gln Gly Gln Glu
             325                 330                 335

Lys Val Phe Leu Ser Ala Ser Lys Glu Ser Ser Ala Asp Val Asn Gln
             340                 345                 350

Gln Tyr Thr Lys Leu Thr Phe Thr Pro Thr Gln Ala Asp Arg Phe Val
     355                 360                 365

Leu Ala Phe Arg Ala Trp Leu Arg Lys Phe Gly Asn Ser Gln Pro Asp
     370                 375                 380

Trp Tyr Gly Ser Pro Ser Gln Asp Ala Leu Pro Ser Thr Val Leu Ser
385                 390                 395                 400

Lys Arg Glu Met Leu Asp Arg Tyr Glu Gln His Thr Leu Lys Cys Ser
                 405                 410                 415

Ser Cys Arg Gly Ala His Lys Ala Phe Gln Thr Leu Gln Lys Val Phe
             420                 425                 430

Met Gly Ala Thr Val Val Phe Gly Ala Thr Ser Gly Ile Pro Ala Asp
             435                 440                 445

Val Gln Leu Arg Ile Leu Leu Gly Ala Gly Ala Leu Val Ser Ala Ala
     450                 455                 460
```

-continued

Leu Ala Tyr Val Phe Tyr Asp Arg Gln Lys His Phe Val Phe Val Asp
465                 470                 475                 480

Tyr Val His Ala Asp Ile Asp
                485

<210> SEQ ID NO 37
<211> LENGTH: 592
<212> TYPE: PRT
<213> ORGANISM: Arabidopsis thaliana

<400> SEQUENCE: 37

Met Glu Asp Pro Asp Ile Lys Arg Cys Lys Leu Ser Cys Val Ala Thr
1               5                   10                  15

Val Asp Asp Val Ile Glu Gln Val Met Thr Tyr Ile Thr Asp Pro Lys
                20                  25                  30

Asp Arg Asp Ser Ala Ser Leu Val Cys Arg Arg Trp Phe Lys Ile Asp
            35                  40                  45

Ser Glu Thr Arg Glu His Val Thr Met Ala Leu Cys Tyr Thr Ala Thr
        50                  55                  60

Pro Asp Arg Leu Ser Arg Arg Phe Pro Asn Leu Arg Ser Leu Lys Leu
65                  70                  75                  80

Lys Gly Lys Pro Arg Ala Ala Met Phe Asn Leu Ile Pro Glu Asn Trp
                85                  90                  95

Gly Gly Tyr Val Thr Pro Trp Val Thr Glu Ile Ser Asn Asn Leu Arg
            100                 105                 110

Gln Leu Lys Ser Val His Phe Arg Arg Met Ile Val Ser Asp Leu Asp
        115                 120                 125

Leu Asp Arg Leu Ala Lys Ala Arg Ala Asp Leu Glu Thr Leu Lys
130                 135                 140

Leu Asp Lys Cys Ser Gly Phe Thr Thr Asp Gly Leu Leu Ser Ile Val
145                 150                 155                 160

Thr His Cys Arg Lys Ile Lys Thr Leu Leu Met Glu Glu Ser Ser Phe
                165                 170                 175

Ser Glu Lys Asp Gly Lys Trp Leu His Glu Leu Ala Gln His Asn Thr
            180                 185                 190

Ser Leu Glu Val Leu Asn Phe Tyr Met Thr Glu Phe Ala Lys Ile Ser
        195                 200                 205

Pro Lys Asp Leu Glu Thr Ile Ala Arg Asn Cys Arg Ser Leu Val Ser
210                 215                 220

Val Lys Val Gly Asp Phe Glu Ile Leu Glu Leu Val Gly Phe Phe Lys
225                 230                 235                 240

Ala Ala Ala Asn Leu Glu Glu Phe Cys Gly Gly Ser Leu Asn Glu Asp
                245                 250                 255

Ile Gly Met Pro Glu Lys Tyr Met Asn Leu Val Phe Pro Arg Lys Leu
            260                 265                 270

Cys Arg Leu Gly Leu Ser Tyr Met Gly Pro Asn Glu Met Pro Ile Leu
        275                 280                 285

Phe Pro Phe Ala Ala Gln Ile Arg Lys Leu Asp Leu Leu Tyr Ala Leu
290                 295                 300

Leu Glu Thr Glu Asp His Cys Thr Leu Ile Gln Lys Cys Pro Asn Leu
305                 310                 315                 320

Glu Val Leu Glu Thr Arg Asn Val Ile Gly Asp Arg Gly Leu Glu Val
                325                 330                 335

Leu Ala Gln Tyr Cys Lys Gln Leu Lys Arg Leu Arg Ile Glu Arg Gly
            340                 345                 350

```
Ala Asp Glu Gln Gly Met Glu Asp Glu Glu Gly Leu Val Ser Gln Arg
        355                 360                 365
Gly Leu Ile Ala Leu Ala Gln Gly Cys Gln Glu Leu Glu Tyr Met Ala
    370                 375                 380
Val Tyr Val Ser Asp Ile Thr Asn Glu Ser Leu Glu Ser Ile Gly Thr
385                 390                 395                 400
Tyr Leu Lys Asn Leu Cys Asp Phe Arg Leu Val Leu Leu Asp Arg Glu
                405                 410                 415
Glu Arg Ile Thr Asp Leu Pro Leu Asp Asn Gly Val Arg Ser Leu Leu
            420                 425                 430
Ile Gly Cys Lys Lys Leu Arg Arg Phe Ala Phe Tyr Leu Arg Gln Gly
        435                 440                 445
Gly Leu Thr Asp Leu Gly Leu Ser Tyr Ile Gly Gln Tyr Ser Pro Asn
    450                 455                 460
Val Arg Trp Met Leu Leu Gly Tyr Val Gly Glu Ser Asp Glu Gly Leu
465                 470                 475                 480
Met Glu Phe Ser Arg Gly Cys Pro Asn Leu Gln Lys Leu Glu Met Arg
                485                 490                 495
Gly Cys Cys Phe Ser Glu Arg Ala Ile Ala Ala Val Thr Lys Leu
            500                 505                 510
Pro Ser Leu Arg Tyr Leu Trp Val Gln Gly Tyr Arg Ala Ser Met Thr
        515                 520                 525
Gly Gln Asp Leu Met Gln Met Ala Arg Pro Tyr Trp Asn Ile Glu Leu
    530                 535                 540
Ile Pro Ser Arg Arg Val Pro Glu Val Asn Gln Gln Gly Glu Ile Arg
545                 550                 555                 560
Glu Met Glu His Pro Ala His Ile Leu Ala Tyr Tyr Ser Leu Ala Gly
                565                 570                 575
Gln Arg Thr Asp Cys Pro Thr Thr Val Arg Val Leu Lys Glu Pro Ile
            580                 585                 590

<210> SEQ ID NO 38
<211> LENGTH: 520
<212> TYPE: PRT
<213> ORGANISM: Zea mays

<400> SEQUENCE: 38

Met Arg Ala Thr Ile Pro Ala Leu Ser Leu Leu Val Thr Pro Arg Leu
1               5                   10                  15
Pro Ser Leu Ala Val Pro Leu Ala Gly Gly Arg Leu Arg Glu Gly Gly
            20                  25                  30
Arg Ser Arg Thr Arg Leu Arg Val Ala Ala Pro Thr Ser Val Pro Gly
        35                  40                  45
Glu Ala Ala Glu Gln Ala Glu Pro Ser Thr Ser Ala Pro Glu Ser Gly
    50                  55                  60
Glu Lys Phe Ser Trp Arg Asp His Trp Tyr Pro Val Ser Leu Val Glu
65              70                  75                  80
Asp Leu Asp Pro Ser Arg Pro Thr Pro Phe Gln Leu Leu Asn Arg Asp
                85                  90                  95
Leu Val Ile Trp Lys Glu Pro Lys Ser Gly Glu Trp Val Ala Leu Asp
            100                 105                 110
Asp Arg Cys Pro His Arg Leu Ala Pro Leu Ser Glu Gly Arg Ile Asp
        115                 120                 125
Glu Thr Gly Cys Leu Gln Cys Ser Tyr His Gly Trp Ser Phe Asp Gly
```

-continued

```
                130                 135                 140
Ser Gly Ala Cys Thr Lys Ile Pro Gln Ala Met Pro Glu Gly Pro Glu
145                 150                 155                 160

Ala Arg Ala Val Arg Ser Pro Lys Ala Cys Ala Ile Lys Phe Pro Thr
                165                 170                 175

Leu Val Ser Gln Gly Leu Leu Phe Val Trp Pro Asp Glu Asn Gly Trp
                180                 185                 190

Glu Lys Ala Ala Ala Thr Lys Pro Pro Met Leu Pro Lys Glu Phe Glu
            195                 200                 205

Asp Pro Ala Phe Ser Thr Val Thr Ile Gln Arg Asp Leu Phe Tyr Gly
            210                 215                 220

Tyr Asp Thr Leu Met Glu Asn Val Ser Asp Pro Ser His Ile Glu Phe
225                 230                 235                 240

Ala His His Lys Val Thr Gly Arg Arg Asp Arg Ala Arg Pro Leu Thr
                245                 250                 255

Phe Arg Met Glu Ser Ser Gly Ala Trp Gly Tyr Ser Gly Ala Asn Ser
                260                 265                 270

Gly Asn Pro Arg Ile Thr Ala Thr Phe Glu Ala Pro Cys Tyr Ala Leu
            275                 280                 285

Asn Lys Ile Glu Ile Asp Thr Lys Leu Pro Ile Phe Gly Asp Gln Lys
            290                 295                 300

Trp Val Ile Trp Ile Cys Ser Phe Asn Ile Pro Met Ala Pro Gly Lys
305                 310                 315                 320

Thr Arg Ser Ile Val Cys Ser Ala Arg Asn Phe Gln Phe Thr Met
                325                 330                 335

Pro Gly Lys Ala Trp Trp Gln Leu Val Pro Arg Trp Tyr Glu His Trp
            340                 345                 350

Thr Ser Asn Leu Val Tyr Asp Gly Asp Met Ile Val Leu Gln Gly Gln
            355                 360                 365

Glu Lys Ile Phe Leu Ala Ala Thr Lys Glu Ser Ser Thr Asp Ile Asn
            370                 375                 380

Gln Gln Tyr Thr Lys Ile Thr Phe Thr Pro Thr Gln Ala Asp Arg Phe
385                 390                 395                 400

Val Leu Ala Cys Arg Thr Trp Leu Arg Lys Phe Gly Asn Ser Gln Pro
                405                 410                 415

Glu Trp Phe Gly Asn Pro Thr Gln Glu Ala Leu Pro Ser Thr Val Leu
            420                 425                 430

Ser Lys Arg Glu Met Leu Asp Arg Tyr Glu Gln Leu Ser Leu Lys Cys
            435                 440                 445

Ser Ser Cys Lys Gly Ala Tyr Asn Ala Phe Gln Asn Leu Gln Lys Val
            450                 455                 460

Phe Met Gly Ala Thr Val Val Cys Cys Ala Ala Gly Ile Pro Pro
465                 470                 475                 480

Asp Val Gln Leu Arg Leu Leu Ile Gly Ala Ala Leu Val Ser Ala
                485                 490                 495

Ala Ile Ala Tyr Ala Phe His Glu Leu Gln Lys Asn Phe Val Phe Val
            500                 505                 510

Asp Tyr Val His Ala Asp Ile Asp
            515                 520
```